(12) United States Patent
Cicerone et al.

(10) Patent No.: US 8,120,772 B2
(45) Date of Patent: Feb. 21, 2012

(54) METHOD FOR NRB-FREE NONLINEAR VIBRATIONAL SPECTROSCOPY AND MISCROSCOPY

(75) Inventors: Marcus T. Cicerone, Urbana, MD (US); Young Jong Lee, Gaithersburg, MD (US)

(73) Assignee: The United States of America as represented by the Secretary of Commerce, the National Institute of Standards and Technology, Washington, DC (US)

( * ) Notice: Subject to any disclaimer, the term of this patent is extended or adjusted under 35 U.S.C. 154(b) by 317 days.

(21) Appl. No.: 12/611,176

(22) Filed: Nov. 3, 2009

(65) Prior Publication Data
US 2010/0110426 A1 May 6, 2010

Related U.S. Application Data

(60) Provisional application No. 61/110,686, filed on Nov. 3, 2008.

(51) Int. Cl.
*G01J 3/44* (2006.01)
(52) U.S. Cl. ....................................................... 356/301
(58) Field of Classification Search .............. 356/72–73, 356/301
See application file for complete search history.

(56) References Cited

U.S. PATENT DOCUMENTS

| | | | |
|---|---|---|---|
| 6,809,814 B2 | 10/2004 | Xie et al. | |
| 7,092,086 B2 | 8/2006 | Knebel | |
| 7,256,885 B2 | 8/2007 | Silberberg et al. | |
| 7,289,203 B2 | 10/2007 | Frankel | |
| 7,352,458 B2 | 4/2008 | Xie et al. | |
| 7,388,668 B2 | 6/2008 | Potma et al. | |
| 7,414,729 B2 | 8/2008 | Xie et al. | |
| 7,474,462 B2 | 1/2009 | Ulrich et al. | |
| 2004/0145735 A1* | 7/2004 | Silberberg et al. | 356/301 |
| 2008/0309931 A1 | 12/2008 | Silberberg et al. | |

FOREIGN PATENT DOCUMENTS
WO 2005116596 A1 12/2005
WO 2006078716 A2 7/2006

OTHER PUBLICATIONS

Y. Liu, Y. J. Lee, M. T. Cicerone, "Broadband CARS spectral phase retrieval using a time-domain Kramers-Kronig transform"; Optics Letters; May 1, 2009; vol. 34, No. 9; 1363-1365.

* cited by examiner

*Primary Examiner* — Gregory J Toatley
*Assistant Examiner* — Abdullahi Nur
(74) *Attorney, Agent, or Firm* — Rankin, Hill & Clark LLP

(57) ABSTRACT

Methods and systems are described for suppressing nonresonant background in broadband coherent anti-Stokes Raman scattering (CARS) microscopy and spectroscopy. The methods and systems improve sensitivity and signal to noise ratio in CARS.

25 Claims, 13 Drawing Sheets

METHOD FOR NRB-FREE NONLINEAR VIBRATIONAL SPECTROSCOPY AND MISCROSCOPY

CROSS REFERENCES TO RELATED APPLICATIONS

This application claims priority from U.S. provisional application Ser. No. 61/110,686 filed on Nov. 3, 2008, herein incorporated by reference.

FIELD OF THE INVENTION

The present invention relates to a method of suppressing nonresonant background (NRB) in broadband coherent anti-Stokes Raman scattering (CARS) microscopy to improve sensitivity and signal-to-noise ratio.

BACKGROUND OF THE INVENTION

Coherent anti-Stokes Raman scattering (CARS) microscopy has been used widely for noninvasive, label-free, three-dimensional chemical imaging of biological and polymeric samples. CARS microscopy is based on third-order nonlinear vibrational spectroscopy. The overall CARS signal is given by:

$$|\chi(\omega)|^2 = |\chi_{NR}|^2 + 2\chi_{NR} Re[\chi_R(\omega)] + |\chi_R(\omega)|^2$$

This signal contains a nonresonant background (NRB), arising from the nonresonant third-order susceptibility ($\chi_{NR}$) and resonant component that is proportional to the square of the third-order resonant susceptibility ($\chi_R$). The signal also contains a "cross term" proportional to the product of the two susceptibilities. The NRB is generated by all molecular species in the sample. The NRB is impulsive, and thus in phase with the excitation field, (i.e., is strictly real). The resonant component is the signal of interest; it is generated only when the frequency difference of excitation fields is close to a resonant vibrational frequency of a molecule in the sample. In contrast to the NRB, the resonant signal has a component that is in phase (real) and one that is out of phase (imaginary) with the excitation field.

There are two major classes of CARS microscopy—single frequency and broadband (or multiplex). Single frequency CARS approaches use two picosecond pulses tuned to a specific Raman mode, exciting only a single vibrational mode, to achieve fast data acquisition speed and high sensitivity. However, quantitative Raman spectrum analysis of complex media including biological samples generally requires information about many vibrational modes, and a wide range of frequency data at a single measurement. Multiplex and broadband CARS approaches have been demonstrated to provide a broad Raman spectrum at a single measurement by overlapping a narrowband picosecond pulse and a broadband pulse. Despite a relatively slow imaging speed, the multiplex measurement techniques show great advantages for analysis of crowded Raman spectra, e.g., in the fingerprint region (typically 400-2000 cm$^{-1}$, and particularly 500-1800 cm$^{-1}$), and in the C-H stretch region (2600-3200 cm$^{-1}$).

The NRB can, and typically does, dominate the signal for single-frequency and broadband CARS approaches. The NRB can be sufficiently strong as to completely overwhelm weak resonant signals, leading to significant reduction in imaging contrast and sensitivity. Thus, the NRB has to be accounted for in signal processing or experimentally eliminated in order to realize the chemical imaging potential of CARS microscopy. In cases where the resonant component of the signal is of intermediate strength or stronger, it may be best to eliminate the NRB by experimental methods, and collect only the resonant component. On the other hand, while the presence of the NRB can obscure the resonant component in the raw CARS signal, the NRB actually amplifies the resonant signal through the presence of the cross term. Thus, when the resonant component is very weak, it may be advantageous to exploit the amplification of the resonant by the nonresonant component by allowing all or some fraction of the NRB to persist, collecting the full CARS signal and using a signal analysis method to separate the resonant and nonresonant contributions.

Several experimental approaches have been developed for reducing or eliminating the NRB contribution. These include frequency-modulation, epi-detection, polarization control, time-resolved, and interference CARS techniques. However, the frequency modulation technique is not currently available for coupling with broadband CARS microscopy. The epi-detection suppresses the contribution of bulk solvent but is applicable to only small features compared to the wavelength of the scattering light. Polarization control and time-resolved CARS techniques can attenuate resonant signals significantly.

Interferometric CARS offers the possibility of detecting an NRB-free CARS signal without attenuation. Interferometric detection methods can provide the real and imaginary response of the third-order nonlinear susceptibility $\chi^{(3)}$ by measuring combined signal of a CARS field from the sample of interest and a well-controlled reference field. Heterodyne methods use a strong reference field (local oscillator) to enhance the resonant signal in addition to separating out the phase information. However, these reference fields are generally generated in a different medium. Under these circumstances it is generally very difficult to account for differential phase shift and differential chirp over a broad frequency range, and to remove phase jitter. Generating signal and reference fields in the same sample obviates these problems. Silberberg et al. as described in D. Oron, N. Dudovich, and Y. Silberberg, Phys. Rev. Lett. 90, (2003), have demonstrated single pulse CARS techniques where NRB is reduced by interfering adjacent narrow spectral components of a single ultrashort laser pulse using a pulse shaper. Since a spatial light modulator controls the whole frequency range of pump, Stokes, and probe fields, the number of elements in the spatial light modulator limits the product of spectral resolution and spectral range. Cicerone et al. as described in T. W. Kee, H. X. Zhao, and M. T. Cicerone, Opt. Express 14, 3631 (2006), have demonstrated a different approach to interferometric broadband CARS microscopy by mixing signal and reference fields that are generated by a spectrally narrow pulse and a broad pulse for pump light, respectively. However, in that approach, it was necessary to scan the phase of one of the probe beams, thereby increasing the data acquisition time.

Several signal analysis methods for accounting for NRB have recently been applied to broadband and multiplex CARS microscopy. These are described in E. M. Vartiainen, H. A. Rinia, M. Muller, and M. Bonn, Opt. Express 14, 3622 (2006); and S. H. Lim, A. G. Caster, and S. R. Leone, Opt. Lett. 32, 1332 (2007). The method of Lim et al. is based on Fourier transform spectral interferometry, and uses a sequence of steps that is equivalent, within an additive factor, to a Kramers-Kronig (KK) method described by Peterson and Knight in C. W. Peterson and B. W. Knight, J. Opt. Soc. Am. 63, 1238 (1973). In the approaches to KK transforms discussed above, the response of interest is assumed explicitly or implicitly to rise like a step function at time=0. However, such a step-function response could be realistic only when 1) the impulse triggering the signal is a delta function and 2) either the real and the imaginary component of the signal is entirely conjugate; or, if a nonconjugate part (e.g., a real-only component) does exist, it is spectrally flat. For CARS, none of these conditions are realized in practice; the probe pulse (the impulse triggering the response) typically has a temporal width similar to the Raman response time, and the complex resonant response is accompanied by a real nonresonant response, carrying a frequency-dependent amplitude that reflects the convolution of the pump and Stokes pulses.

Although various techniques have been described or proposed for reducing or accounting for nonresonant background (NRB) in coherent anti-Stokes Raman scattering (CARS) applications, a need remains for further reducing and/or accounting for such NRB.

SUMMARY OF THE INVENTION

The difficulties and drawbacks associated with previously described techniques are overcome in the present methods and systems for CARS analyses.

In a first aspect, the present invention provides a system for producing a coherent anti-Stokes Raman scattering (CARS) signal associated with a medium. The system comprises an array for producing a first optical pulse composed of a pump field and a Stokes field; and a second optical pulse composed of a probe field. The system further comprises a first element for pulse-shaping the second optical pulse to suppress nonresonant background contribution to CARS. The system also comprises a second element for directing the first and second optical pulses to a focal volume of a medium such that a CARS signal is produced. And, the system additionally comprises a detector for detecting a separated CARS signal from the focal volume in the medium.

In another aspect, the present invention provides a method for producing a coherent anti-Stokes Raman scattering (CARS) signal associated with a medium. The method comprises producing a first optical pulse carrying a pump field and a Stokes field. The method also comprises producing a second optical pulse carrying a probe field. The method further comprises shaping the second optical pulse to suppress nonresonant background contribution to CARS and produce a shaped second optical pulse. The method also comprises directing the first optical pulse and the shaped second optical pulse to a focal volume to produce a CARS signal. And, the method comprises detecting the separated CARS signal from the focal volume in the medium.

In another aspect, the present invention provides a method for manipulating the time-domain representation of the CARS signal to account for non-ideality in the CARS response, including a frequency-dependent nonresonant background (NRB). In this method, the assumptions typically made in order to apply a KK transform are relaxed, including the constraint of step-function signal rise, thereby allowing accounting for the real nonresonant response.

As will be realized, the invention is capable of other and different embodiments and its several details are capable of modifications in various respects, all without departing from the invention. Accordingly, the drawings and description are to be regarded as illustrative and not restrictive.

BRIEF DESCRIPTION OF THE DRAWINGS

FIG. 12 (b) illustrates a temporal function obtained by a modified time-domain constraint. The inset of FIG. 12 (b) illustrates a temporal function, obtained without NRB information. FIG. 12 (c) (top) illustrates extracted Raman spectrum (solid) and a reference Raman spectrum (dashed). And, FIG. 12 (c) (bottom) illustrates a difference between the reference and retrieved Raman spectra. FIG. 12 (c) inset illustrates Raman spectrum extracted using the temporal function from the inset of FIG. 12 (b).

FIG. 13 (b) illustrates Raman spectrum extracted using equations (16) and (17) and the separately measured background.

DETAILED DESCRIPTION OF THE EMBODIMENTS

Figure 1:
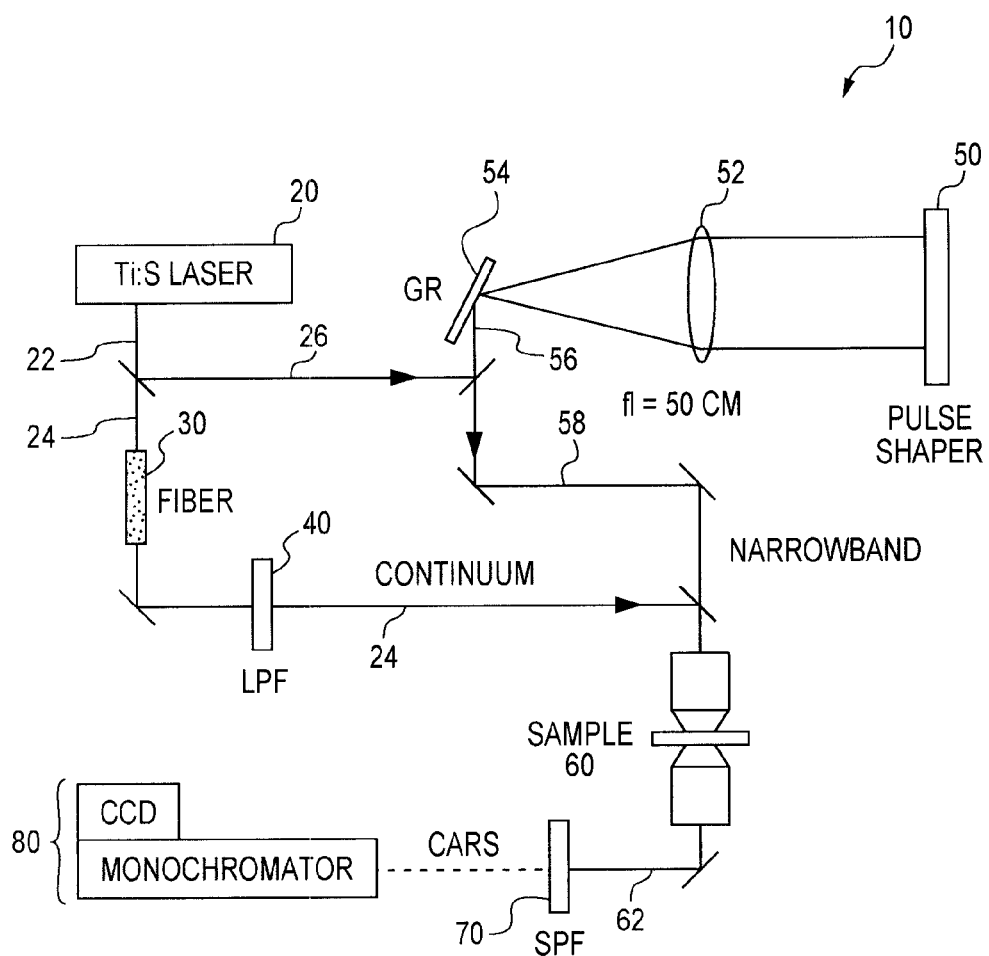
FIG. 1 is a schematic illustration of a preferred embodiment single shot interference broadband CARS microscopy system.

The present invention provides various methods and systems for producing optical pulses to induce a nonlinear spectroscopy process in a medium. The present invention also provides a mathematical signal processing approach for extracting real and imaginary components of signal(s) associated with the nonlinear process. The invention is particularly related to the field of coherent anti-Stokes Raman scattering (CARS) spectroscopy and microscopy. The present invention provides inducing a CARS process by exciting the medium with two optical pulses. One of the pulses is a transform-limited broad pulse that is composed of pump and Stokes fields. The other pulse is a pulse-shaped signal that is composed of a probe field. The present invention provides various optimization techniques directed to the probe pulse to produce a resonant CARS signal free of nonresonant background (NRB) contribution which has been a major obstacle for CARS microscopy. The optimization techniques associated with the probe pulse comprise dispersing a probe pulse in a pulse shaper and determining the intensity and phase of individual frequency components of the probe pulse.

The present invention also provides various methods and strategies for shaping a probe pulse for suppression of NRB without losing resonant CARS signals. As described in greater detail herein, a strategy for shaping a probe pulse comprises: (1) splitting the input optical pulse into multiple spectral groups with non-zero electric field amplitude envelops; (2) determining the relative phases of the multiple spectral groups as either zero degree (in-phase) or 180 degrees (out-of-phase) to each other; and (3) determining the intensities of the multiple spectral groups to satisfy the condition that the integration of the electric field envelope of the shaped probe pulse on the frequency domain becomes zero. The previously described shaping technique can be implemented by passing a single probe pulse through a dual-mask spatial light modulator (SLM), which can change both amplitude and phase of individual pixels on its masks. Alternatively or additionally, the shaping can be facilitated by locating proper neutral density filters, beam blockers, and/or glass windows in the pulse shaper. As examples, the present invention provides two types of shaping of a probe pulse: ps-ps scheme and ps-fs scheme. The ps-fs scheme comprises two transform-limited groups that are located at the same center frequency and have different bandwidths and amplitudes. One has a narrow spectral bandwidth, such as from about 1 to about 10 $cm^1$ and the other has a broad spectral bandwidth of from about 50 to about 500 $cm^{-1}$ and their phase difference is 180 degrees. The ps-ps scheme comprises two transform-limited groups that have the same bandwidths and amplitudes but having center frequencies which are separated from each other. The bandwidth is from about 1 to about 10 $cm^{-1}$ and the center frequencies are separated by about 2 to about 30 $cm^{-1}$ and their phase difference is 180 degrees.

The present invention further provides methods of applying a mathematical signal processing approach for separating the real and imaginary components of the CARS spectrum, and thus isolating the resonant component of the signal from the nonresonant background (NRB).

As previously explained, the NRB limits sensitivity and chemical image contrast of CARS microscopy especially in the fingerprint region, which contains most of molecular specific Raman information of biological systems. The presence of NRB also limits sensitivity and chemical contrast in the C-H stretch region—another very important spectral region for biological systems. However, the NRB is difficult to remove and characterize. Even though several approaches have been established for reducing or accounting for the NRB contribution, most of the methods accompany either resonant signal reduction by orders of magnitude, distortion of spectral features by vibrational mode dynamics and morphology, or invalid assumptions about how the signal is generated. The present invention utilizes a uniquely optimized probe pulse in a single-laser, two-pulse, three-color CARS system, providing unique capabilities such as, but not limited to, (1) complete suppression of the NRB contribution, (2) great acquisition efficiency of resonant signals, (3) high signal-to-noise-ratio Raman spectra, (4) recovery of Raman spectra insensitive to Raman dephasing time, depolarization ratio, and spatial morphology, (5) broad spectral range, including the fingerprint region (typically 400 $cm^{-1}$ to 2000 $cm^{-1}$, and particularly 500 $cm^{-1}$ to 1800 $cm^1$), and in the C-H stretch region (2600-3200 $cm^{-1}$). (6) compatibility with other CARS techniques, and (7) microscopy imaging capability. The present invention also utilizes a mathematical innovation that allows a correct resonant signal to be obtained from the overall CARS signal, even in the presence of a strong NRB.

In accordance with the invention, various preferred embodiment systems are provided as described in greater detail herein. Generally, the preferred embodiment systems include an array for producing various optical pulses, and for analyzing signals arising from optical pulses. Typically, a first optical pulse which carries a pump field and a Stokes field is produced. And, a second optical pulse carrying a probe field is produced. An example of a device or system for producing such pulses is a suitably configured laser. The first optical pulse is preferably provided by continuum generation from an optical fiber. The first optical pulse preferably has a spectral bandwidth of at least 2000 $cm^{-1}$. The first optical pulse can in certain systems and/or techniques, be compressed such that the first pulse exhibits a pulse duration in the range of from about 5 to about 100 femtoseconds.

The preferred systems also include a pulse shaper and a controller for appropriately shaping the second optical pulse. This is performed to suppress nonresonant background (NRB) contribution to CARS. The controller serves to control phases and intensities of individual frequency components of the second optical pulse. The controller may be in a multitude of different forms and configurations. For example, the controller may include a spatial light modulator through which the second optical pulse is directed. The controller may include an optical medium that changes optical phases of specific frequency components of the second optical signal. For example, the optical medium may be a phase compensating glass plate having a thickness for example of from about 0.01 mm to about 3 mm. The phase of the specific frequency components of the second optical signal can be determined by rotation of the glass plate. The controller may include a neutral density filter having a predetermined optical density in the range of 0 to 2 for example.

The system also includes an element for directing the first and second optical pulses to a focal volume of a medium so that a CARS signal is produced.

And, the system further includes a detector for detecting a separated CARS signal from the focal volume of the medium.

In accordance with the invention, various preferred embodiment methods are provided as described in greater detail herein. Generally, the methods comprise producing a first optical pulse which carries a pump field and a Stokes field. As previously noted, a laser can be used to produce this pulse.

The preferred embodiment methods also comprise producing a second optical pulse that carries a probe field. As previously noted, a laser can be used to produce this pulse.

The preferred embodiment methods also include an operation in which the second optical pulse is shaped in order to suppress nonresonant background contribution to CARS. Shaping of the second pulse can be accomplished by directing the second pulse through a pulse shaper and controlling phases and intensities of individual frequency components of the second optical pulse. The phases and intensities of individual frequency components of the second pulse can be controlled by (i) dividing the input optical pulse into multiple spectral groups, (ii) setting the relative phases of the multiple spectral groups to either zero (in-phase) or 180 degrees (out of phase) with respect to each other, and (iii) modifying the intensities of the multiple spectral groups to make the sum of the electric field envelopes of the multiple spectral groups become zero. The controlling of phases and intensities of individual frequency components of the second pulse can include passing a pulse through a spatial light modulator. Further controlling of phases and intensities of individual frequency components of the second pulse may include passing the pulse through an optical medium that changes optical phases of specific frequency components of the second pulse. For example, the optical medium may be in the form of a phase compensating glass plate having a representative thickness of from about 0.01 mm to about 3 mm. The phase of specific frequency components can be determined by rotating the glass plate. Moreover, controlling of phases and intensities of individual frequency components of the second pulse can include passing the pulse through a neutral density filter having a predetermined optical density in the range of from about 0 to about 2 for example. The controlling operation may also include blocking fractions of the light at unwanted or undesired frequency ranges.

The previously noted multiple spectral groups preferably comprise two transform-limited groups that are located at the same center frequency and have different bandwidths and amplitudes (ps-fs scheme). One group has a narrow spectral bandwidth of from about 1 cm$^{-1}$ to about 10 cm$^{-1}$. And, the other group has a broad spectral bandwidth of from about 50 cm$^{-1}$ to about 500 cm$^{-1}$, wherein their phase difference is 180 degrees. The previously noted multiple spectral groups can comprise two transform-limited groups that have the same bandwidths and amplitudes, but which have center frequencies that are separated from each other (ps-ps scheme). The bandwidth is from about 1 cm$^{-1}$ to about 10 cm$^{-1}$ and the center frequencies are separated by from about 2 cm$^{-1}$ to about 30 cm$^{-1}$. The two groups are out of phase from each other by 180 degrees.

The preferred embodiment methods also include an operation of directing the first optical pulse and the second optical pulse to a focal volume to produce a CARS signal.

And, the preferred embodiment methods include an operation of detecting the separated CARS signal from the focal volume in the medium.

The preferred embodiment methods also include modifying the pulse sequence to allow some or all of the NRB to survive in the CARS signal in order to amplify a weak nonresonant signal through the cross term. In this embodiment, the resonant component of the signal is extracted through signal analysis by applying a Kramers-Kronig-based transform that accounts for the non-impulse response of the CARS by allowing for nonzero amplitude in the negative-time component of the temporal representation of the CARS spectrum.

The preferred embodiment of the signal analysis method involves obtaining the time-domain representation of the full CARS signal and a nonresonant background signal by Fourier transform or other means. The positive-time component of the time-domain full CARS signal is added to the negative-time component of the time-domain NRB signal. The composite time-domain representation is transformed back to the frequency domain, and the imaginary part is taken as the equivalent of the resonant Raman spectrum.

FIG. 1 schematically illustrates a single shot interference broadband CARS microscopy system 10. The system 10 comprises a Titanium Sapphire (Ti:S) laser 20, which emits a light beam 22. After splitting of the beam into first and second beams 24 and 26 respectively, one of the beams 24 is passed through a photonic crystal fiber (PCF) 30 and then directed to a longpass filter (LPF) 40. The other beam 26 is combined with shaped light pulses 56 from a pulse shaper 50 after the pulses pass one or more optical elements 52 and a grating element (GR) 54. The resulting combined beam 58 is then combined with the previously noted beam 24 and then directed to a sample. The light 62 from the sample region is passed through a short-pass filter (SPF) 70 after which CARS analysis can be performed by a detector and/or suitable processing equipment 80. FIG. 1 is described in greater detail herein.

Figure 2A:
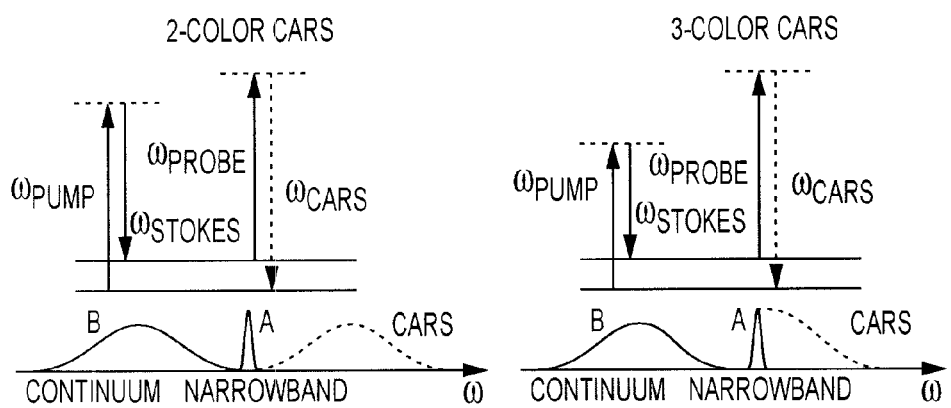
FIG. 2(a) illustrates schematic diagrams of 2- and 3-color CARS generation mechanisms in two-pulse broadband CARS spectroscopy. CARS spectra are depicted in FIG. 2(b) for 2-color and FIG. 2(c) for 3-color mechanisms.
Figure 2B:
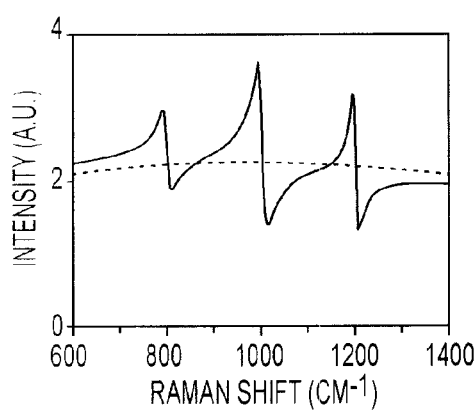
Figure 2C:
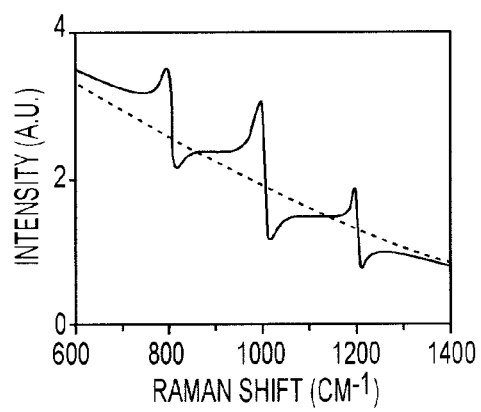

FIG. 2 shows (a) schematic diagrams of 2- and 3-color CARS generation mechanisms in two-pulse broadband CARS spectroscopy. Solid lines A indicate transitions induced by a narrowband pulse; solid lines B, by a continuum pulse; and dashed lines indicate induced CARS emission. CARS spectra are simulated as shown in FIG. 2(b) for 2-color and FIG. 2(c) for 3-color mechanisms. The dashed lines indicate NRB contribution.

The CARS signal is induced by the third-order nonlinear polarization, $P^{(3)}$, which is expressed as:

$$P^{(3)}(\omega_{aS}) = \int_{-\infty}^{\infty}\int_{-\infty}^{\infty}\int_{-\infty}^{\infty} \chi^{(3)} E(\omega_p) E(\omega_S)^* E(\omega_{pr}) \delta(\omega_p - \omega_S + \omega_{pr} - \omega_{aS}) d\omega_p d\omega_S d\omega_{pr} \quad (1)$$

where $\chi^{(3)}$ the third-order nonlinear susceptibility, $E^\omega$ are the electric field vectors, and the subscripts p, pr, S and aS indicate pump, Stokes, probe, and anti-Stokes transitions, respectively. A broadband CARS signal can be generated by two different generation mechanisms as described in FIG. 2: (i) "2-color" CARS, where the pump and probe are provided by a narrowband pulse, and the continuum pulse constitutes the Stokes light; and (ii) "3-color" CARS, where pump and Stokes are provided by two different frequency components in the continuum pulse and the narrowband pulse serves as probe. Depending on the generation mechanism, the nonlinear polarization for CARS emission has different expressions as follows:

$$P_{2\text{-}color}^{(3)}(\omega_{aS}) = \int_{-\infty}^{\infty}\int_{-\infty}^{\infty} \chi^{(3)} E_n(\omega_p) E_c^*(\omega_S) E_n(\omega_{pr}) dw_p dw_{pr} \quad (2)$$

$$P_{3\text{-}color}^{(3)}(\omega_{aS}) = \int_{-\infty}^{\infty}\int_{-\infty}^{\infty} \chi^{(3)} E_c(\omega_p) E_c^*(\omega_S) E_n(\omega_{pr}) dw_p dw_{pr} \quad (3)$$

where $E_n(\omega)$ and $E_c(\omega)$ are the electric fields of the narrowband and continuum pulses, and $\omega_{aS} = \omega_p - \omega_S + \omega_{pr}$. The nonlinear polarizations and electric fields are treated as scalar values for simplicity. In broadband CARS spectroscopy, $\chi^{(3)}$ can be described as a function of $(\omega_{pr} - \omega_{aS})$ and can be expressed using parameters for a spontaneous Raman spectrum as follows:

$$\chi^{(3)}(\omega_{aS}, \omega_{pr}) = \chi_{NR}^{(3)} + \chi_R^{(3)}(\omega_{aS}, \omega_{pr}) \quad (4)$$

$$= \chi_{NR}^{(3)} + \sum_i \frac{A_i}{[(\omega_{aS} - \omega_{pr}) - \Omega_{R,i}] + i\Gamma_i}$$

where $\chi_{NR}^{(3)}$ and $\chi_R^{(3)}$ are the nonresonant and resonant contributions, respectively, $\Omega_{R,i}$ is the frequency of the ith Raman mode, $A_i$ is a constant representing the spontaneous Raman cross section, and $\Gamma_i$ is the Raman linewidth. Then, equations (2) and (3) can be rewritten as:

$$P_{2\text{-}color}^{(3)}(\omega_{aS}) = \int_{-\infty}^{\infty} E_n(\omega_p) E_c^*(\omega_S) d\omega_p \int_{-\infty}^{\infty} \chi^{(3)}(\omega_{aS}, \omega_{pr}) E_n(\omega_{pr}) d\omega_{pr} \quad (5)$$

$$P_{3\text{-}color}^{(3)}(\omega_{aS}) = \int_{-\infty}^{\infty} E_c(\omega_p) E_c^*(\omega_S) d\omega_p \int_{-\infty}^{\infty} \chi^{(3)}(\omega_{aS}, \omega_{pr}) E_n(\omega_{pr}) d\omega_{pr} \quad (6)$$

The 3-color and 2-color CARS signals differ in several ways. One difference is that the 3-color signal always displays amplitude that decreases with increasing Raman shift due to the frequency-domain autocorrelation of the continuum pulse, expressed in the first integral on the right hand side of equation (6). Another difference, is that the 2-color signal is generated with two photons from the narrow-band pulse, whereas 3-color uses only one photon. As explained in greater detail herein, this means that all 2-color signals vanish under the same conditions required for NRB suppression.

Two model cases are demonstrated herein in which a narrowband pulse $E_n(\omega)$ is modified into a superposition of two pulse components whose amplitudes and phases are independently controllable. In case (1) "ps-fs", two Gaussian pulses have different bandwidths and are located at the same center frequency. In case (2) "ps-ps", two Gaussian pulses have the same bandwidths and the center frequencies are separated from each other. In both model cases, the resulting CARS spectra show a strong interferometric behavior with regard to the relative phase between the two pulse components. Both cases are described using both analytical expressions and simulations of spectra. In the spectral simulations, a Raman spectrum is utilized with three peaks centered at $\Omega_{R,1}=800$ cm$^{-1}$, $\Omega_{R,2}=1000$ cm$^{-1}$ and $\Omega_{R,3}=1200$ cm$^{-1}$, with amplitudes $A_1=A_3=0.5$, and $A_2=1$, and widths $\Gamma_1=\Gamma_2=10$ cm$^{-1}$ and $\Gamma_3=5$ cm$^{-1}$. It is also assumed that $\chi_{NR}^{(3)}=0.2$. FIG. 2 shows simulated 2- and 3-color CARS spectra. In all simulations, the full-width-half-maximum (FWHM) of the narrowband pulse is set to be 5 cm$^{-1}$ and the FWHM of the continuum pulse is set to be 2500 cm$^{-1}$. Both the narrowband and continuum pulses are assumed to be transform-limited Gaussian functions.

In the ps-fs scheme, $E_n(\omega)$ consists of two Gaussian pulses $E_{ps}(\omega)$ and $E_{fs}(\omega)$, where the bandwidths are significantly different but center frequencies are the same. The electric fields of the two Gaussian pulses are expressed as:

$$E_{ps}(\omega)=E_{ps}^0 \exp[-(2\ln 2)\times(\omega-\omega_c)^2/\Delta\omega_{ps}^2] \text{ and}$$

$$E_{fs}(\omega)=E_{fs}^0 \exp[-(2\ln 2)\times(\omega-\omega_c)^2/\Delta\omega_{fs}^2]$$

where $E_{ps}^0$ and $E_{fs}^0$ are the peak field amplitudes, $\omega_c$ is the center frequency, and $\Delta\omega_{ps}$ and $\Delta\omega_{fs}$ are the FWHM of the intensity spectra. The overall electric field of the narrowband pulse can be written as:

$$E_n(\omega)=E_{ps}(\omega)e^{i\Delta\phi}+E_{fs}(\omega) \quad (7)$$

where $\Delta\phi$ is the phase difference between the two pulses. Expressions for 2-color or 3-color CARS emission intensity, $I(\omega_{aS}) \propto |P^{(3)}(\omega_{aS})|^2$, induced by $E_{ps}(\omega)$ and $E_{fs}(\omega)$ are obtained by combining equation (7) with equation (5) or (6), respectively:

$$I_{ps-fs}^{2-color}(\omega_{aS}, \Delta\phi) \propto \quad (8)$$

$$\left| E_c^*(\omega_S) \int_{-\infty}^{\infty} [E_{ps}(\omega_p)e^{i\Delta\phi} + E_{fs}(\omega_p)]d\omega_p \times \int_{-\infty}^{\infty} \chi^{(3)}(\omega_{aS}, \omega_{pr})[E_{ps}(\omega_{pr})e^{i\Delta\phi} + E_{fs}(\omega_{pr})]d\omega_{pr}\right|^2$$

$$I_{ps-fs}^{3-color}(\omega_{aS}, \Delta\phi) \propto \quad (9)$$

$$\left| \int_{-\infty}^{\infty} E_c(\omega_p)E_c(\omega_S)^* d\omega_p \int_{-\infty}^{\infty} \chi^{(3)}(\omega_{aS}, \omega_{pr})[E_{ps}(\omega_{pr})e^{i\Delta\phi} + E_{fs}(\omega_{pr})]d\omega_{pr}\right|^2$$

The NRB contribution to the signal can be determined by replacing $\chi^{(3)}$ with $\chi_{NR}^{(3)}$ (a frequency-independent constant) in equations (8) and (9). Interference between the signals generated from $E_{ps}(\omega)$ and $E_{fs}(\omega)$ results in strong dependence of NRB intensity on both $\Delta\phi$ and $E_{fs}^0/E_{ps}^0$.

Figure 3A:
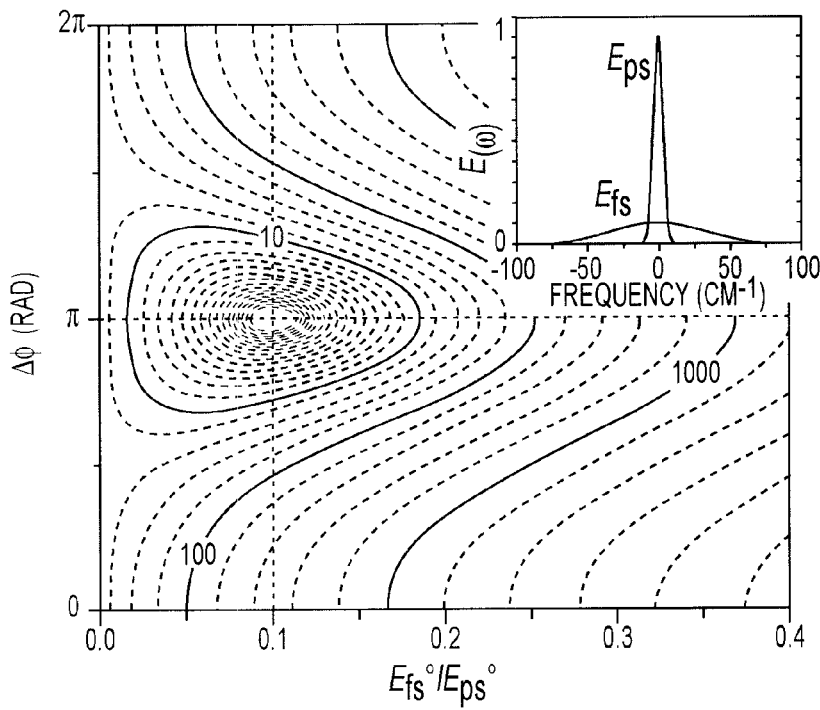
FIG. 3(a) is a log-scale contour plot of simulated NRB intensity as a function of $\Delta\phi$ and $E_{fs}^0/E_{ps}^0$ in 2-color CARS in the ps-fs scheme.
Figure 3B:
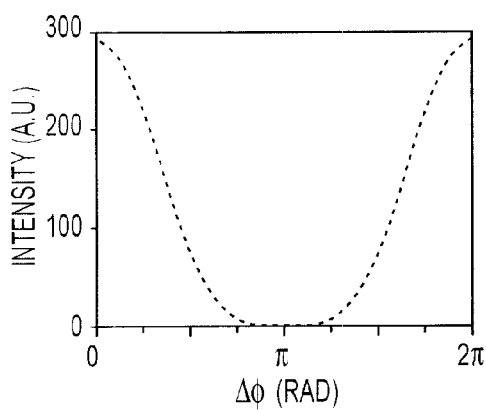
FIG. 3(b) is a linear plot of the vertical line scan in FIG. 3(a).
Figure 3C:
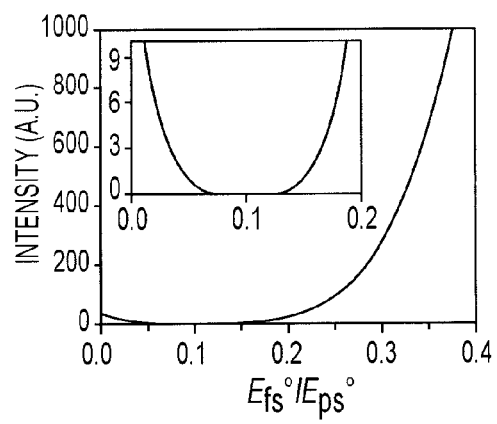
FIG. 3(c) is a linear plot of the CARS intensity.

FIG. 3(a) shows 2-color NRB intensity as a function of $\Delta\phi$ and $E_{fs}^0/E_{ps}^0$ for $E_n(\omega)$ with $\Delta\omega_{ps}=5$ cm$^{-1}$ and $\Delta\omega_{fs}=50$ cm$^{-1}$. The inset of FIG. 3(a) shows an example $E_n(\omega)$ composed of $E_{ps}(\omega)$ and $E_{fs}(\omega)$. For any given value of $E_{fs}^0/E_{ps}^0$, the NRB contribution is minimized at $\Delta\phi=\pi$ (out-of-phase). It is completely suppressed only when $\Delta\phi=\pi$ and $\int_{-\infty}^{\infty}E_{ps}(\omega)d\omega=\int_{-\infty}^{\infty}E_{fs}(\omega)d\omega$; i.e., for $\Delta\omega_{fs}/\Delta\omega_{ps}=10$, $E_{fs}^0/E_{ps}^0=0.1$. Specifically, FIG. 3(a) is a log-scale contour plot of simulated NRB intensity as a function of $\Delta\phi$ and $E_{fs}^0/E_{ps}^0$ in 2-color CARS in the ps-fs scheme. The inset shows the electric fields $E_{ps}(\omega)$ and $E_{fs}(\omega)$ where $\Delta\omega_{ps}=5$ cm$^{-1}$ and $\Delta\omega_{ps}=50$ cm$^{-1}$, respectively. FIG. 3(b) is a linear plot of the vertical line scan in FIG. 3(a), where $E_{fs}^0/E_{ps}^0=0.1$. FIG. 3(c) is a linear plot of the CARS intensity at $\Delta\phi=\pi$ as a function of $E_{fs}^0/E_{ps}^0$, where the intensity is normalized by one at $\Delta\phi=0$.

Figure 4A:
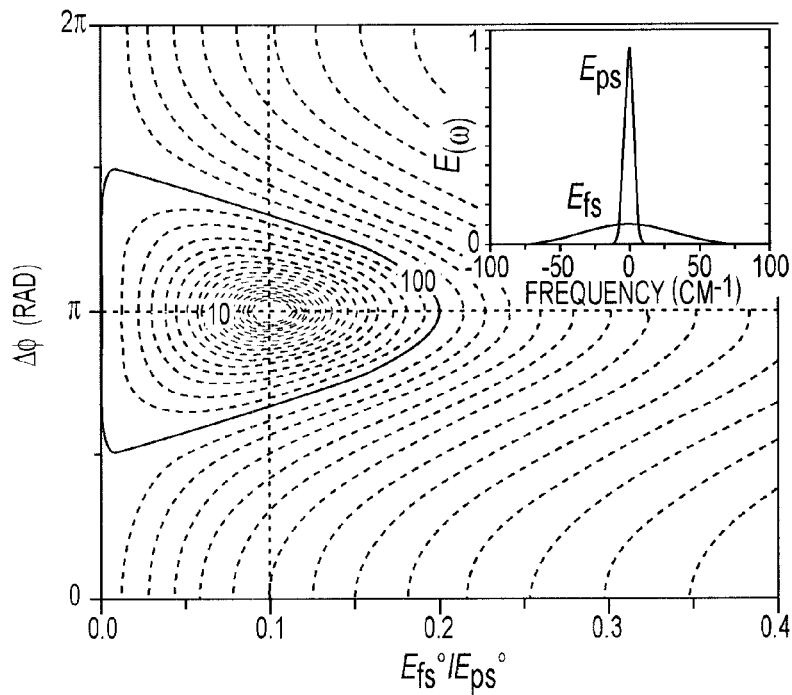
FIG. 4(a) is a log-scale contour plot of simulated NRB intensity as a function of $\Delta\phi$ and $E_{fs}^0/E_{ps}^0$ in 3-color CARS in the ps-fs scheme.
Figure 4B:
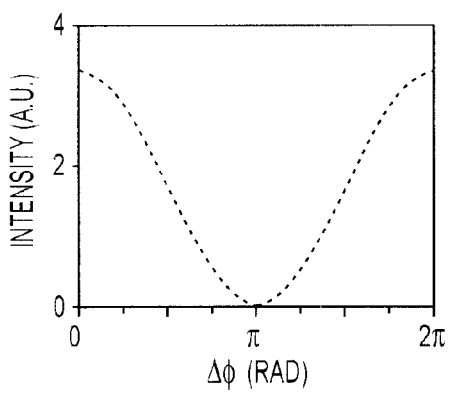
FIG. 4(b) is a linear plot of the vertical line scan in FIG. 4(a).
Figure 4C:
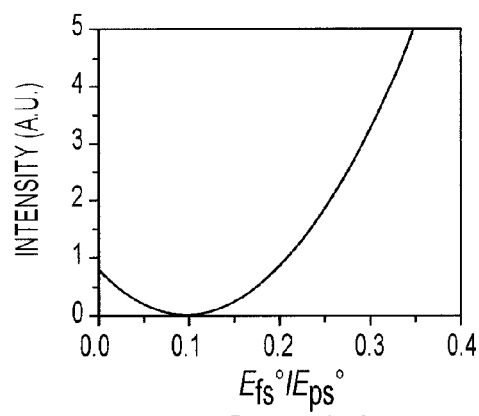
FIG. 4(c) is a linear plot of the CARS intensity.

FIG. 4 shows 3-color NRB intensity as a function of $\Delta\phi$ and $E_{fs}^0/E_{ps}^0$ and the NRB contribution is completely suppressed at $\Delta\phi=\pi$ and $\int_{-\infty}^{\infty}E_{ps}(\omega)d\omega=\int_{-\infty}^{\infty}E_{fs}(\omega)d\omega$ as in at 2-color NRB. Specifically, FIG. 4(a) shows a log-scale contour plot of simulated NRB intensity as a function of $\Delta\phi$ and $E_{fs}^0/E_{ps}^0$ in 3-color CARS in the ps-fs scheme. The inset of FIG. 4(a) shows the electric fields $E_{ps}(\omega)$ and $E_{fs}(\omega)$ where $\Delta\omega_{ps}=5$ cm$^{-1}$ and $\Delta\omega_{fs}=50$ cm$^{-1}$, respectively. FIG. 4(b) is a linear plot of the vertical line scan in (a), where $E_{fs}^0/E_{ps}^0=0.1$. And, FIG. 4(c) is a linear plot of the CARS intensity at $\Delta\phi=\pi$ as a function of $E_{fs}^0/E_{ps}^0$, where the intensity is normalized by one at $\Delta\phi=0$.

Inspection of equation (8) immediately shows that the entire 2-color signal vanishes when the NRB is suppressed since the first integral term on in the equation)°becomes zero regardless of $\chi^{(3)}(\omega_{aS},\omega_{pr})$. Therefore, a single-shot NRB-free 2-color CARS spectrum is not available by the ps-fs interference scheme. For 3-color CARS signal, on the other hand, the integral term of $E_{ps}(\omega)$ and $E_{fs}(\omega)$ in equation (9) can have a non-zero value due to $\chi^{(3)}(\omega_{aS},\omega_{pr})$ in the integral. In the CARS signal generated using such a pulse, the resonant Raman peak features generated by $E_{fs}(\omega)$ are smeared out, yielding an approximately flat spectrum, while the line shape of resonant Raman peaks generated by $E_{ps}(\omega)$ is sharp and dispersive, characteristic of CARS spectra. The NRB generated by $E_{fs}(\omega)$ and $E_{ps}(\omega)$ will cancel because the phase of the signals due to each are out of phase by $\pi$. The resonant signal from the former only slightly attenuates the resonant signal from the latter due to the flat line shape of the $E_{fs}(\omega)$-derived signal. Under these conditions, the surviving signal is composed primarily of contributions from the resonant CARS signal due to the ps pulse.

Figure 5A:
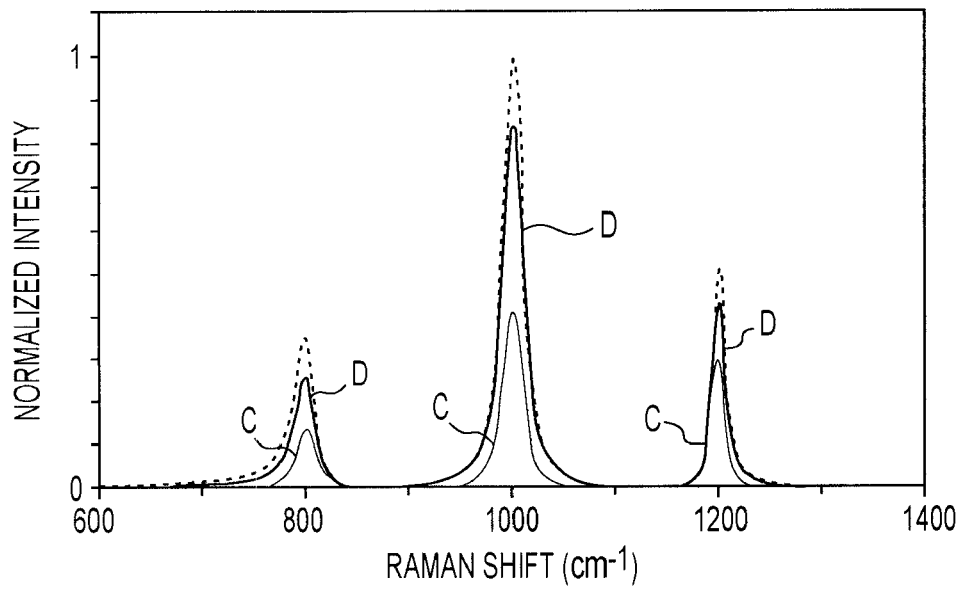
FIG. 5(a) illustrates an NRB suppressed 3-color CARS spectra in the ps-fs scheme for two different $\Delta\omega_{fs}$.
Figure 5B:
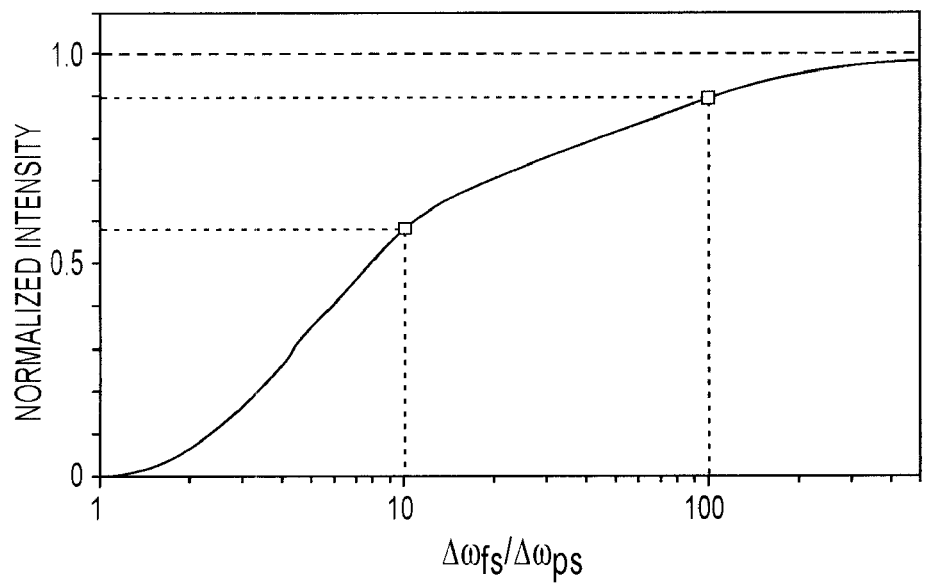
FIG. 5(b) is a semi-log plot of normalized peak intensity of the Raman mode at 1000 cm$^{-1}$ as a function of $\Delta\omega_{fs}$.

FIG. 5(a) illustrates NRB suppressed 3-color CARS spectra in the ps-fs scheme for two different $\Delta\omega_{fs}$ of 50 cm$^{-1}$ (line C) and 500 cm$^{-1}$ (line D) when $\Delta\omega_{ps}=5$ cm$^{-1}$. The dotted line is the 3-color CARS spectrum calculated only with resonant signal $|\chi_{NR}^{(3)}=0|$ generated by a ps pulse. FIG. 5(b) is a semi-log plot of normalized peak intensity of the Raman mode at 1000 cm$^{-1}$ as a function of $\Delta\omega_{fs}$ while $\Delta\phi=\pi$ and $E_{fs}^0/E_{ps}^0=\Delta\omega_{ps}/\Delta\omega_{fs}$. More specifically, FIG. 5(a) shows 3-color CARS spectra calculated using this NRB elimination scheme, with $\Delta\omega_{ps}=5$ cm$^{-1}$ and $\Delta\omega_{fs}=50$ cm$^{-1}$ and 500 cm$^{-1}$. The resonant peak intensity of $\Delta\omega_{fs}=500$ cm$^{-1}$ is larger than that of $\Delta\omega_{fs}=50$ cm$^{-1}$. The $\Delta\omega_{fs}$ dependence of resonant peak intensity is shown more noticeably in FIG. 5(b), where the peak intensity of the Raman mode at 1000 cm$^{-1}$ is plotted as a function of increasing $\Delta\omega_{fs}/\Delta\omega_{ps}$, with $\Delta\omega_{ps}$ fixed at 5 cm$^{-1}$. The peak intensity asymptotically increases with $\Delta\omega_{fs}/\Delta\omega_{ps}$ towards 100% recovery of the pure nonresonant signal, which can be calculated with $\chi_{NR}^{(3)}=0$ and $E_n(\omega)$ composed only of $E_{ps}(\omega)$. In the frequency domain, as $\Delta\omega_{fs}$ increases, resonant signal feature from $E_{fs}(\omega)$ becomes close to flat and, the sharp peaks by $E_{ps}(\omega)$ survives. In the time domain, the NRB suppression condition, $\int_{-\infty}^{\infty}[E_{ps}(\omega_p)e^{i\Delta\phi}+E_{fs}(\omega_p)]d\omega_p$, makes the peak power the same for variable $\Delta\omega_{fs}$ pulses but the pulse duration reduced by $(\Delta\omega_{fs})-1$. Since the response time of NRB is almost instantaneous, the NRB signal generated by the fs pulse is the same value with the opposite sign, compared with the NRB signal by the out-of-phase ps pulse. However, the response time of a resonant CARS signal is much slower than the fs pulse but close to the ps pulse, so the resulting resonant CARS signal is mostly due to the ps pulse. Therefore, the NRB-free 100% resonant CARS signal by a ps pulse can be achieved by interfering a same peak power fs pulse with $\Delta\omega_{fs}$ⓇΔω. The dotted line is a spectrum calculated with $\chi_{NR}^{(3)}=0$ and $E_n(\omega)$ composed only of $E_{ps}(\omega)$, as a reference showing the maximum amplitude obtainable without amplification due to mixing with the NRB. For example, in FIG. 5(b), $\Delta\omega_{fs}=50$ cm$^{-1}$ and 500 cm$^{-1}$, the peak intensities of the Raman mode at 1000 cm$^{-1}$ reach 59% and 90%, respectively, of the pure resonant CARS intensity. It should be noted that this large amount of resonant signal recovery is very difficult to achieve by other NRB suppression techniques such as polarization control and epi-detection techniques. Furthermore, in principle, this interference approach can be coupled with those other techniques to improve chemical or morphological selectivity.

Figure 6A:
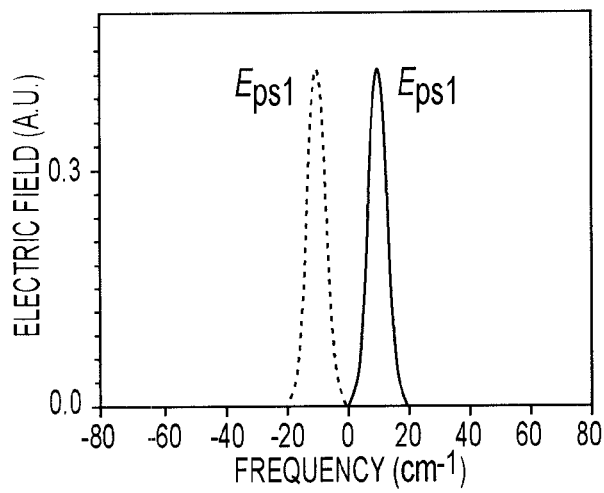
FIG. 6(a) illustrates $E_{ps1}(\omega)$ and $E_{ps2}(\omega)$ used in the ps-ps scheme.
Figure 6B:
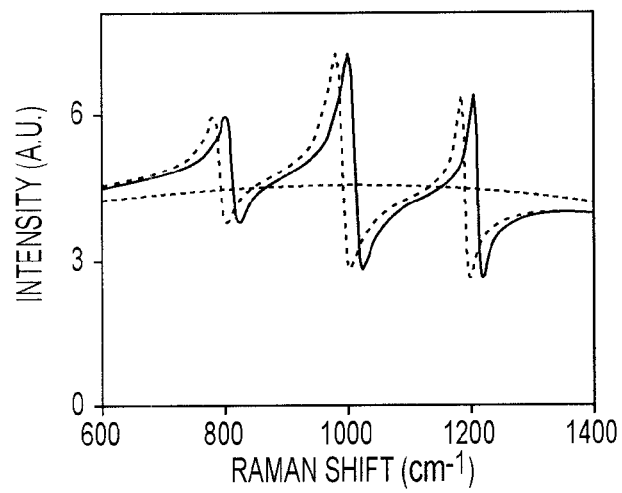
FIG. 6(b) depicts 2-color CARS spectra calculated with the two ps pulses of FIG. 6(a).
Figure 6C:
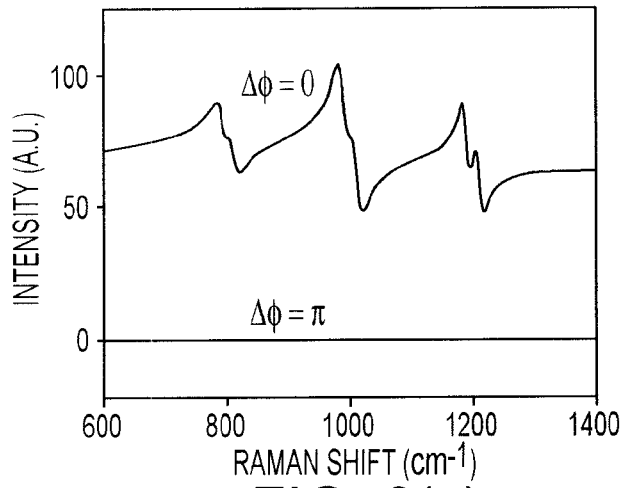
FIG. 6(c) illustrates NRB intensity calculated for 2-color CARS in the ps-ps scheme as a function of the phase shift, $\Delta\phi$, and the frequency shift, $\Delta\omega_c$.

FIG. 6(a) shows $E_{ps1}(\omega)$ and $E_{ps2}(\omega)$ used in the ps-ps scheme where $\Delta\omega_c=20$ cm$^{-1}$ and $\Delta\omega_{ps}$ of 5 cm$^{-1}$. FIG. 6(b) illustrates 2-color CARS spectra calculated with the two ps pulses of FIG. 6(a). The dashed line indicates CARS spectra calculated by replacing $\chi^{(3)}$ with $\chi_{NR}^{(3)}$. FIG. 6(c) shows NRB intensity calculated for 2-color CARS in the ps-ps scheme as a function of the phase shift, $\Delta\phi$, and the frequency shift, $\Delta\omega_c$. And, more specifically, in the ps-ps scheme, $E_n(\omega)$ consists of two picosecond Gaussian pulses whose bandwidths are the same but their center frequencies are shifted, as shown in FIG. 6(a). The electric fields of the picosecond pulses can be expressed as:

$$E_{ps1}(\omega)=E_{ps}^0 \exp[-(2\ln 2)\times(\omega-\omega_c+\Delta\omega_c/2)^2/\Delta\omega_{ps}^2]$$

and $$E_{ps2}(\omega)=E_{ps}^0 \exp[-(2\ln 2)\times(\omega-\omega_c+\Delta\omega_c/2)^2/\Delta\omega_{ps}^2],$$

where $\Delta\omega_c$ is the frequency separation between the two pulses. FIG. 6(b) shows the 2-color CARS spectra calculated with $E_{sp1}(\omega)$ and $E_{sp2}(\omega)$, respectively. The overall electric field of the narrowband pulse is thus written as:

$$E_p(\omega)=E_{ps1}(\omega)e^{i\Delta\phi}+E_{ps2}(\omega) \qquad (10)$$

Expressions for the 2-color or 3-color CARS signal intensity in the ps-ps scheme are then obtained by combining equation (10) with equation (5) or (6), respectively:

$$I_{ps-ps}^{2-color}(\omega_{aS},\Delta\phi) \propto \qquad (11)$$

$$\left| E_c^* \int_{-\infty}^{\infty} [E_{ps1}(\omega_p)e^{i\Delta\phi} + E_{ps2}(\omega_p)]d\omega_p \times \int_{-\infty}^{\infty} \chi^{(3)}(\omega_{aS},\omega_{pr})[E_{ps1}(\omega_{pr})e^{i\Delta\phi} + E_{ps2}(\omega_{pr})]d\omega_{pr} \right|^2$$

$$I_{ps-ps}^{3-color}(\omega_{aS},\Delta\phi) \propto \qquad (12)$$

$$\left| \int_{-\infty}^{\infty} E_c(\omega_p)E_c(\omega_S)^* d\omega_p \int_{-\infty}^{\infty} \chi^{(3)}(\omega_{aS},\omega_{pr})[E_{ps1}(\omega_{pr})e^{i\Delta\phi} + E_{ps2}(\omega_{pr})]d\omega_{pr} \right|^2$$

As with the previous scheme, NRB is completely suppressed and the 2-color signal also vanishes as shown in FIG. 6(c) when $\int_{-\infty}^{\infty}[E_{ps1}(\omega_p)e^{i\Delta\phi}+E_{ps2}(\omega_p)]d\omega_p=0$. In this scheme, the criterion is fulfilled when $\Delta\phi=\pi$, irrespective of the value of $\Delta\omega_c$, as long as the NRB does not change significantly over the interval $\Delta\omega_c$.

Figure 7:
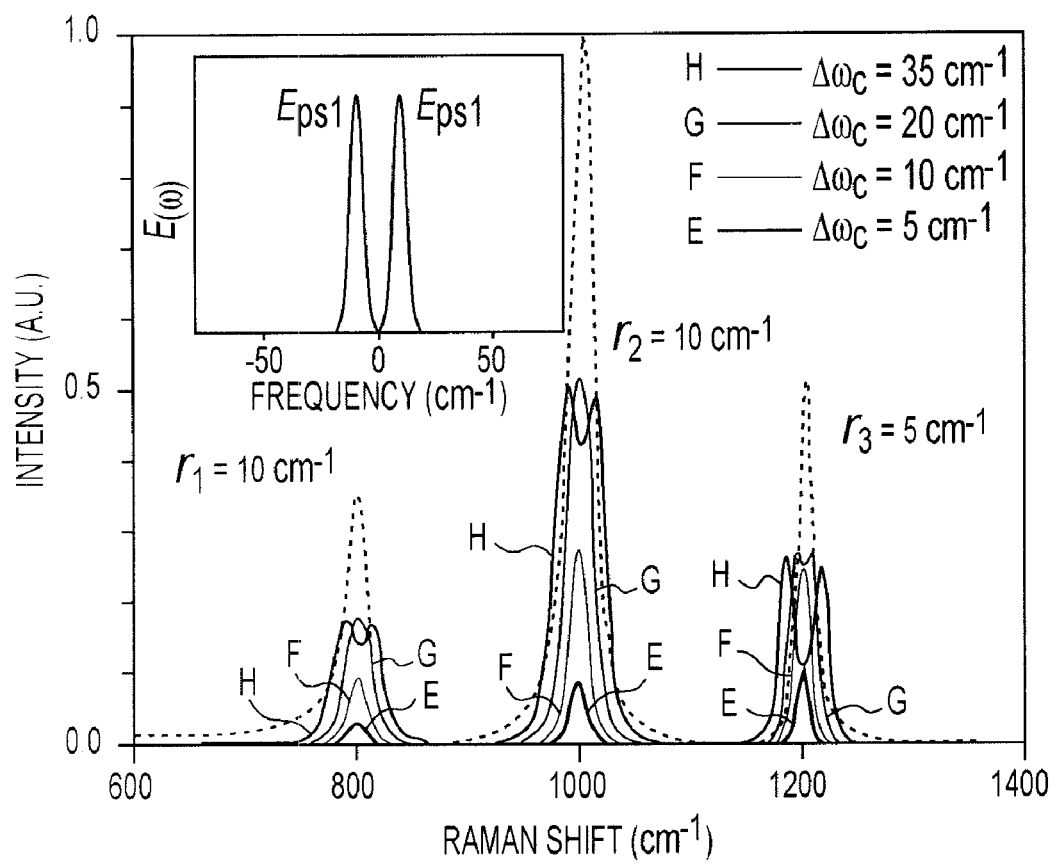
FIG. 7 illustrates simulated 3-color CARS spectra for various $\Delta\omega_c$.

FIG. 7 shows simulated 3-color CARS spectra for various $\Delta\omega_c$. The inset of FIG. 7 shows the electric fields $E_{ps1}(\omega)$ and $E_{ps2}(\omega)$ used in the ps-ps scheme, where $\Delta\omega_c=20$ cm$^{-1}$ and $\Delta\omega_{ps}$ of 5 cm$^{-1}$. As a reference (the dotted line), a 3-color CARS spectrum is calculated for $\chi_{NR}^{(3)}=0$ by a singled ps pulse for $E_n\omega$ when the pulse energy is assumed to be equal to the sum of those of $E_{ps1}(\omega)$ and $E_{ps2}(\omega)$ for the other ps-ps simulations. More specifically, FIG. 7 shows 3-color CARS spectra calculated for $\Delta\phi=\pi$ and various values of $\Delta\omega_c$. The smallest amplitude signal (line E) in FIG. 7 was calculated with and $\Delta\omega_c=\Delta\omega_{ps}$. As $\Delta\omega_c$ is increased (lines F, G and H), the signal intensity increases and the widths of resonant peaks become broader. However, beyond a certain value, there is no further increase in signal amplitude, and a peak splitting artifact emerges, as clearly demonstrated by the spectral peak at 1200 cm$^{-1}$.

Figure 8:
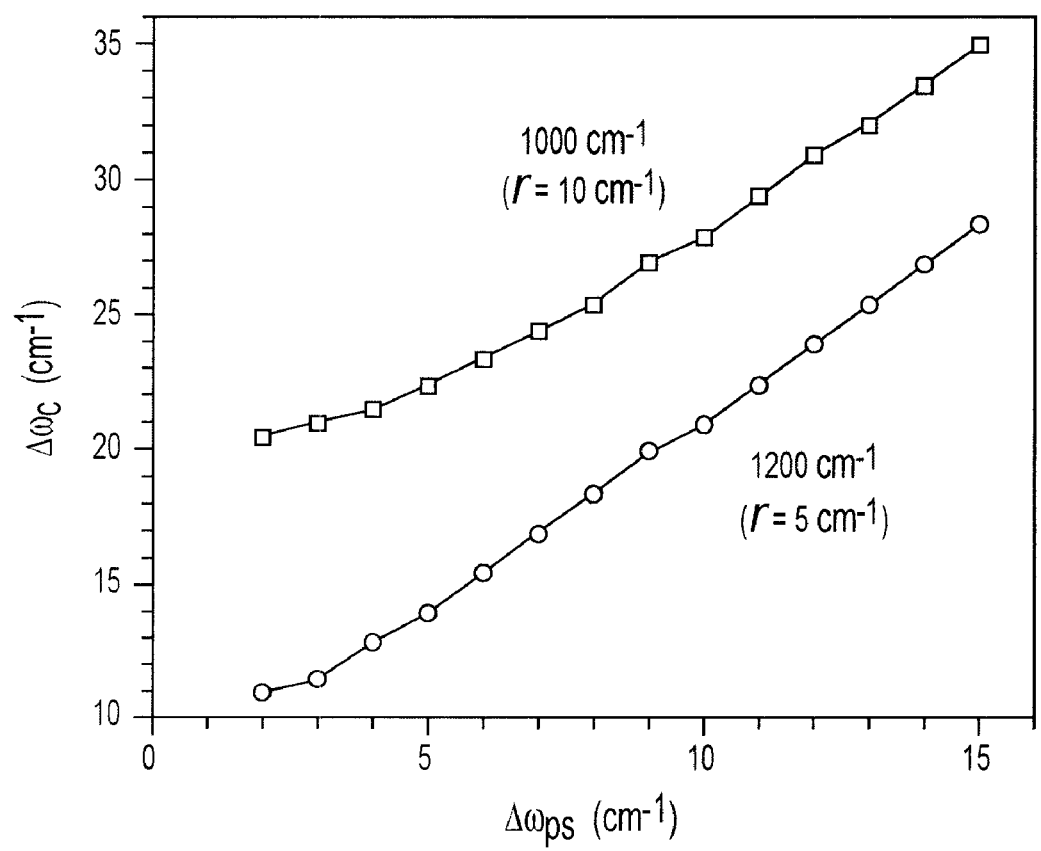
FIG. 8 illustrates frequency shift, $\Delta\omega_c$, versus pulsewidth, $\Delta\omega_{ps}$, for maximum 3-color CARS intensities at $\Delta\phi=\pi$ for two peaks at 1000 cm$^{-1}$ and 1200 cm$^1$.

FIG. 8 shows pulse shift, $\Delta\omega_c$, versus pulsewidth, $\Delta\omega_{ps}$, for the maximum 3-color CARS intensities at $\Delta\phi=\pi$ for two the peaks at 1000 cm$^{-1}$ and 1200 cm$^{-1}$, whose linewidths are set to be 10 cm$^{-1}$ and 5 cm$^{-1}$, respectively. More specifically, FIG. 8 shows the $\Delta\omega_c$ values for the maximum resonant peak intensities plotted as a function of $\Delta\omega_{ps}$ for the two Raman modes. The values are close to twice the FWHM of the non-interferometric spectral feature, i.e. $2[\Gamma^2+(\Delta\omega_{ps})^2]^{1/2}$. The maximum peak intensity in the ps-ps scheme is close to 100% of the pure resonant [$\chi_{NR}^{(3)}=0$] CARS intensity calculated with one of two separated ps pulses. If the pure resonant for [$\chi_{NR}^{(3)}=0$] CARS intensity by a single ps pulse with the same pulse energy as the sum of the $E_n(\omega)$ pulses is used as a reference, the maximum peak intensity corresponds to 50% of the reference in the absence of NRB. There is approximately a 10-fold increase in signal to be gained by manipulating $\Delta\omega_c$ compared to the approach demonstrated by Silberburg et al.

Figure 9:
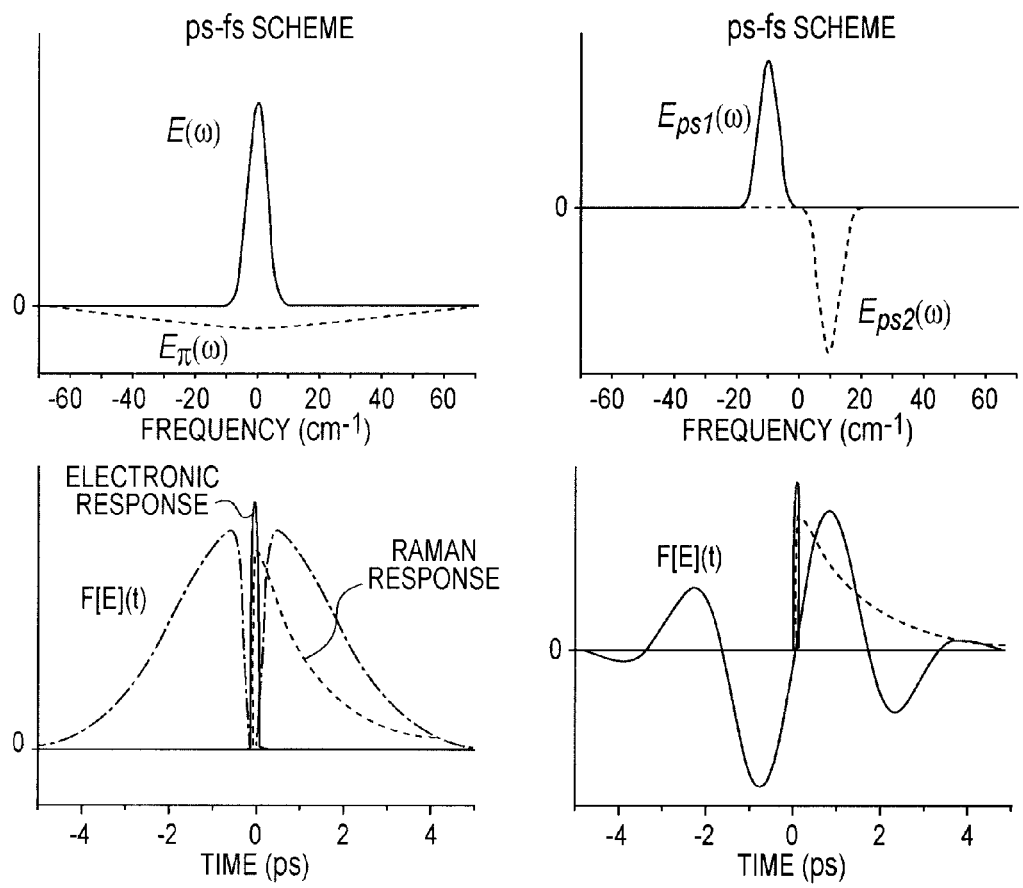
FIG. 9 illustrates electric field amplitudes of ps-fs and ps-ps schemes in the frequency and time domains under NRB suppression conditions.

This single shot interferometric approach can be discussed in the time domain. Referring to FIG. 9, these plots illustrate electric field amplitudes of ps-fs and ps-ps schemes in the frequency and time domains in NRB suppression conditions. For the ps-ps scheme, $\Delta\omega_{ps}$=5 cm$^{-1}$ and $\Delta\omega_{fs}$=50 cm$^{-1}$. For the ps-ps scheme, $\Delta\omega_{ps}$=5 cm$^{-1}$ and $\Delta\omega_c$=20 cm$^{-1}$. More specifically, FIG. 9 shows the Fourier transformed electric field amplitudes of probe pulses, F[E$_n$](t), used for the ps-fs and ps-ps schemes in the NRB suppression conditions. The NRB suppression condition, $\int_{-\infty}^{\infty}[E_1(\omega_p)-E_3(\omega_p)]d\omega_p=0$, is equivalent to F[E$_1$−E$_2$](t)=F[E$_n$](t)=0 at t=0. For both of the schemes, the electric field amplitude is zero at t=0, when a continuum pulse (pump/Stokes) arrives. A continuum pulse generates both electronic and vibrational responses, which are responsible for NRB and resonant CARS contributions, respectively. The former is instantaneous and its response function must be as short as the pulse duration of the transform-limited broadband continuum. On the other hand the Raman response function decays with a time coefficient of a Raman dephasing time, which typically ranges several hundreds femtoseconds to several picoseconds. As FIG. 9 shows, in the NRB suppression conditions, the temporal overlap between F[E$_n$](t) and the electronic response function for NRB contribution becomes negligible compared with that between F[E$_n$](t) and the Raman response function. This makes the NRB free CARS spectrum available in the 3-color broadband CARS spectroscopy. It should be noted that the NRB becomes zero when the continuum pulse is transform-limited, which is very difficult to achieve from a fiber. It has been observed that the photonic crystal fiber has multiple modes with higher order dispersion. A transform-limited continuum pulse could not only make it possible to remove NRB contribution but significantly increase signal intensity of a 3-color CARS spectrum.

The preferred embodiment system depicted in FIG. 1 is based on a two-pulse broadband CARS scheme. Briefly, the output (150 fs, centered at 767 nm, 76 MHz) of a Ti:Sapphire laser oscillator was split into two parts. One part was introduced into a photonic crystal fiber (Femtowhite, Crystal Fibre) to generate a continuum. The remaining oscillator output was introduced into a 4f pulse shaper, where a reflecting spatial light modulator (CRI, SLM-640-D-NM) controlled both amplitude and phase of each frequency pixel. The dispersion on the spatial light modulator was 1.7 cm$^{-1}$/pixel at 767 nm. The pulse shaped for a specific interference scheme was used as a probe pulse. The continuum and probe beams were introduced co-linearly and with parallel polarization into a 1.3 NA oil immersion objective lens. The generated CARS signal was analyzed using a CCD spectrometer (PhotonMax, Roper Scientific).

Figure 10A:
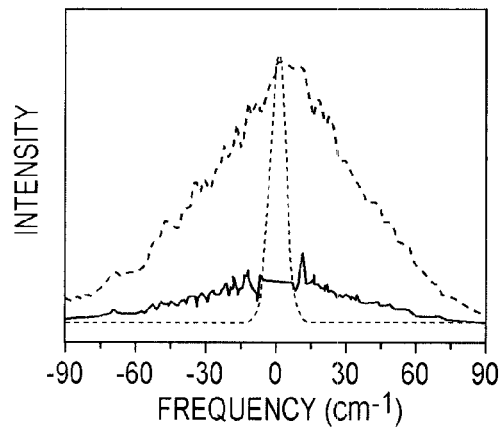
FIG. 10(a) illustrates that the measured spectrum of a single narrowband pulse is decomposed into two Gaussian pulses with $\Delta\omega_{ps}=10$ cm$^{-1}$ and $\Delta\omega_{fs}=97$ cm$^{-1}$ for the ps-fs scheme.
Figure 10B:
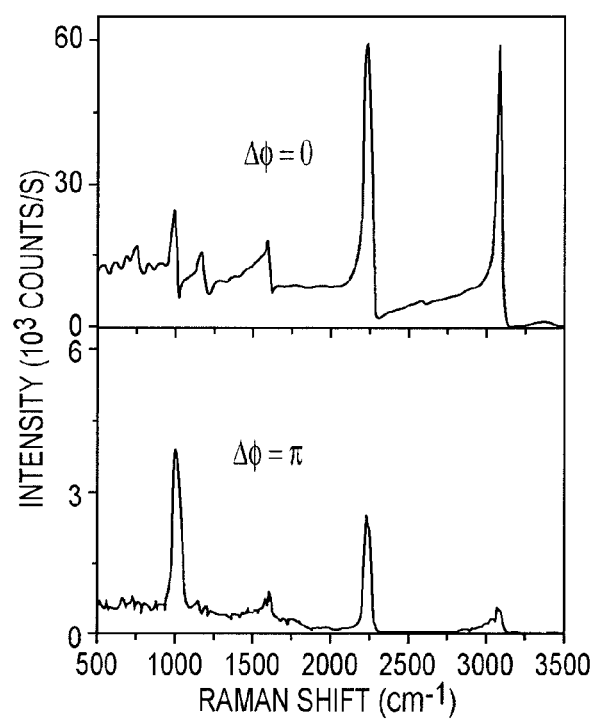
FIG. 10(b) illustrates measured broadband CARS spectra of benzonitrile at $\Delta\phi=0$ and $\pi$.

Generally, FIG. 10(a) depicts the measured spectrum of the single narrowband pulse as decomposed into two Gaussian pulses with $\Delta\omega_{ps}$=10 cm$^{-1}$ and $\Delta\omega_{fs}$=97 cm$^{-1}$ for the ps-fs scheme. FIG. 10(b) illustrates measured broadband CARS spectra of benzonitrile at $\Delta\phi$=0 and π. The laser powers of the narrowband pulse and the continuum pulse are 5.8 mW and 2.4 mW at the sample position. The exposure time is 50 ms. Specifically, FIG. 10(a) shows the narrowband pulse for the ps-fs interference scheme shaped by controlling the amplitude and phase of the original femtosecond pulse (the dotted line) using the spatial light modulator. The phase of the narrow center region (the ps component) is controlled with respect to the phase of the other broad and low intensity region (the fs component). FIG. 10(b) illustrates measured broadband CARS spectra of $\Delta\phi$=0 and π.

Several observations should be noted as follows. First of all, the NRB is significantly reduced in the out-of-phase ($\Delta\phi=\pi$) CARS spectrum as the calculation predicts. Secondly, the peaks at resonant frequencies become symmetrical in the NRB suppressed CARS spectrum, which could help quantitative analysis of crowded Raman spectrum of complex media. Thirdly, peaks at higher Raman shifts are reduced more in the NRB suppressed spectrum. This is consistent with the simulation results of 2- and 3-color interference CARS and the characteristics of 2- and 3-color CARS signals. Only 3-color resonant CARS signals survive at the NRB suppressing condition in the ps-fs interference scheme. 3-color CARS contributes greater to measured CARS signal at lower Raman shifts while 2-color CARS signal is dominant at higher Raman shift (see FIG. 2). It must be noted that the small surviving NRB at low frequency is likely due to the fact that the spatial light modulator (SLM) used in these investigations was not antireflection coated for the wavelength range used, and thus complete suppression of stray reflections was not possible, and due to practical difficulty in satisfying the amplitude condition for complete NRB suppression, $E_{fs}^0/E_{ps}^0=\Delta\omega_{ps}/\Delta\omega_{fs}$. The condition is to match the integrals of the "electric field" spectra of two pulse components, not the "intensity" spectra. For $\Delta\omega_{fs}/\Delta\omega_{ps}$=10, the intensity ratio $I_{fs}^0/I_{ps}^0=(E_{fs}^0/E_{ps}^0)^2$=0.01. However, it is very difficult to control the amplitude by better than 1% using a liquid crystal spatial light modulator. One should expect that increase in $I_{fs}^0/I_{ps}^0$ or decrease in $\Delta\omega_{ps}/\Delta\omega_{fs}$ will cause decrease in resonant signal intensity, as shown in FIG. 3. However, in an optimized system, this problem could be minimized, for example, by inserting a set of additional neutral density filters in the pulse shaper.

Figure 11A:
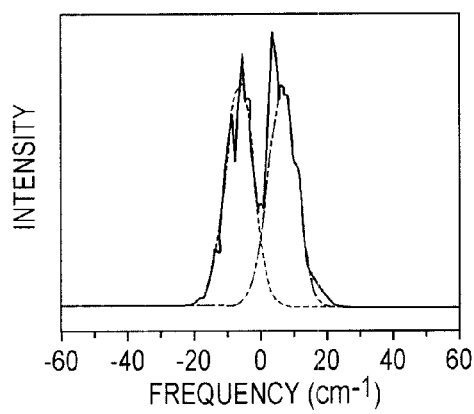
FIG. 11(a) illustrates the measured spectrum of the narrowband pulse for the ps-ps scheme.
Figure 11B:
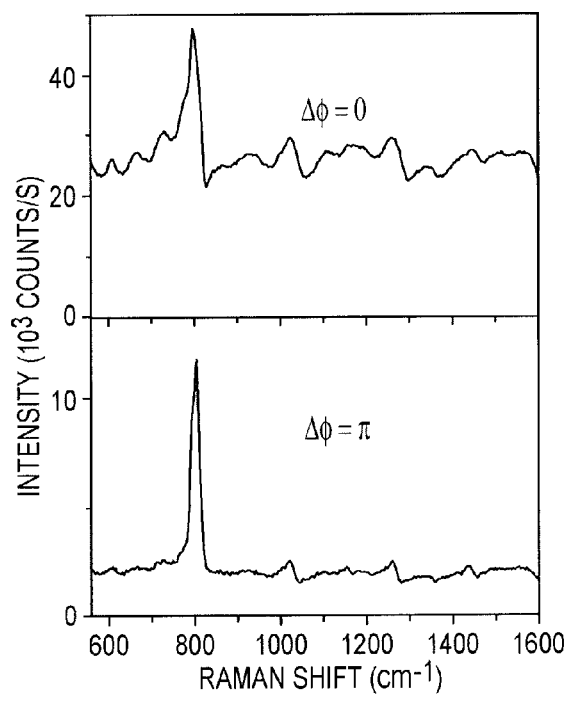
FIG. 11(b) shows measured broadband CARS spectra of c-hexane as a result of interference between the two ps pulses.

FIG. 11(a) shows the measured spectrum of the narrowband pulse for the ps-ps scheme. Fitting the spectrum leads to two Gaussian pulses with $\Delta\omega_{ps}$ of 11 cm$^{-1}$ and $\Delta\omega_c$ of 13 cm$^{-1}$. FIG. 11(b) illustrates measured broadband CARS spectra of c-hexane as a result of interference between the two ps pulses. The vertical lines in the lower plot indicate spontaneous Raman resonant frequencies. The laser powers of the narrowband pulse and the continuum pulse are 7 mW and 6 mW at the sample position. As will be appreciated, FIG. 11(a) is the spectrum of a narrowband pulse used to test the ps-ps interference scheme. The phases of the two spectral components are independently controlled and the other spectral fraction is physically blocked to remove possible contributions from unwanted reflections. The measured interference CARS spectrum of c-hexane shows features consistent with simulations, such as significantly reduced NRB contribution and relatively high peak intensity at lower Raman shift. The incomplete suppression of the NRB contribution could be caused by deviation from the amplitude condition, i.e., the intensity integrals of the two pulses should be the same. The frequency resolution of the current pulse shaper is 1.7 cm$^{-1}$, which makes it difficult to control the amplitudes of the two picosecond pulses of 11 cm$^{-1}$ width. As with the previous case, this is a technological issue and could be overcome in an optimized system by taking better advantage of the potential frequency resolution of the pulse shaper; illuminating the full width of the SLM active area.

In the embodiment wherein the pulses are modified to allow some or all of the NRB to be generated and collected along with the resonant spectrum, the resonant spectrum is separated from the NRB via a time-domain modification of a Kramers-Kronig (KK) transform. Set forth below is a demonstration as to how the time-domain representation of the signal can be manipulated to account for nonideality in the CARS response, including a frequency-dependent nonresonant background (NRB). For convenience in developing this idea, an operator is defined as follows:

$$\Psi(f(\omega))=\Im[u(t)\Im^{-1}[f(\omega)]], \tag{13}$$

where $\mathcal{J}$ and $\mathcal{J}^{-1}$ denote Fourier transform and inverse Fourier transform, respectively. Based on the convolution theorem, equation (13) can be rewritten as:

$$\psi(f(\omega)) = \frac{1}{\sqrt{2\pi}} \mathcal{J}[u(t)] * \mathcal{J}[\mathcal{J}^{-1}[f(\omega)]] = \frac{1}{\sqrt{2\pi}} \mathcal{J}[u(t)] * f(\omega), \quad (14)$$

where * denotes convolution. The Fourier transform of the Heaviside function (u(t)) can be expressed as $\mathcal{J}[u(t)]=1/i\sqrt{2\pi}\omega+\sqrt{\pi/2}\delta(\omega)$. Substituting into equation (14) and writing out the convolution integral explicitly, the following is obtained:

$$\psi(f(\omega)) = \frac{1}{2}\left[\frac{-i}{\pi} P \int_{-\infty}^{+\infty} \frac{f(\omega')}{\omega' - \omega} d\omega' + f(\omega)\right] \quad (15)$$

Combining equation (15) with an integral definition of a KK transform:

$$\varphi(\omega) = -\frac{P}{\pi} \int_{-\infty}^{+\infty} \frac{\ln|\chi(\omega'')|}{\omega'' - \omega} d\omega''$$

the following expression is obtained for the phase as a function of the signal modulus:

$$\varphi(\omega) = \frac{-1}{\pi} P \int_{-\infty}^{+\infty} \frac{\ln|\chi(\omega')|}{\omega' - \omega} d\omega' \quad (16)$$

$$= 2\text{Im}\left\{\psi(\ln|\chi(\omega)|) - \frac{\ln|\chi(\omega)|}{2}\right\}.$$

The benefit of representation in equation (16) is that it can be conveniently used to deal with nonideality directly, in the time domain, as demonstrated below.

Figure 12A:
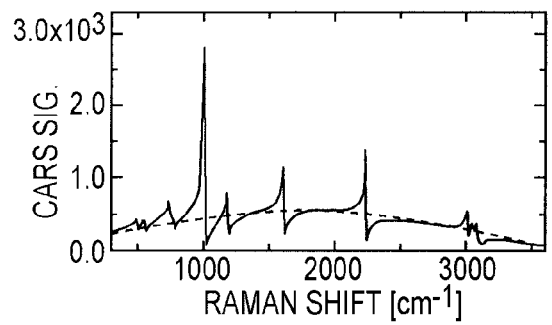
FIG. 12 (a) illustrates numerical simulation of a CARS spectrum via a coherent addition of multiple Lorentzian lineshape functions and a variable nonresonant background (dashed).
Figure 12B:
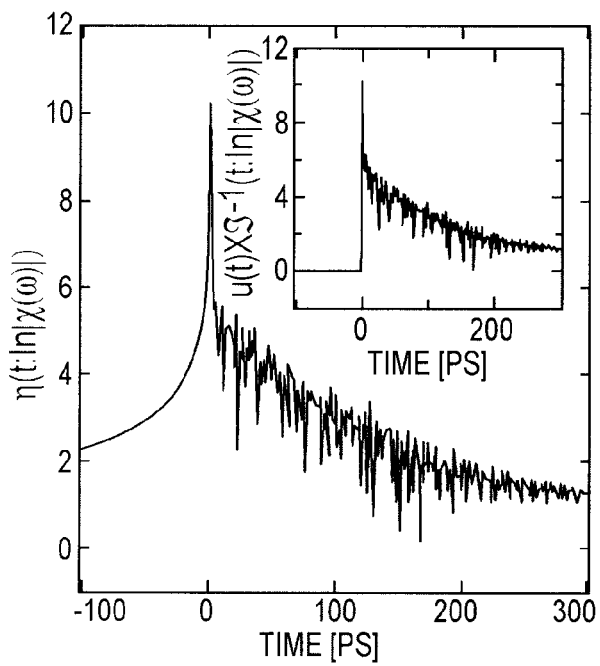
Figure 12C:
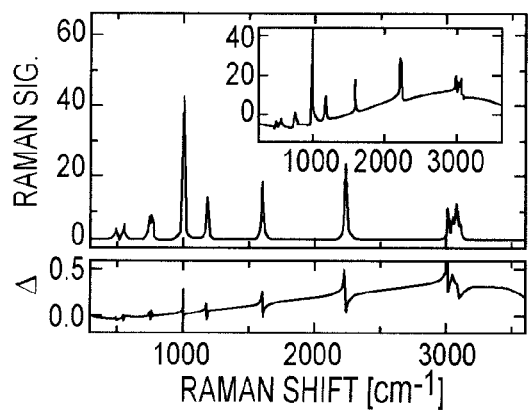

FIG. 12 (a) illustrates numerical simulation of a CARS spectrum via a coherent addition of multiple Lorentzian lineshape functions and a variable nonresonant background (dashed). More specifically, FIG. 12 (a) shows a simulated CARS spectrum with a frequency-dependent NRB amplitude. The simulated signal is computed with the resonant susceptibility calculated as a sum of Lorentzian functions, and a nonresonant amplitude that is not spectrally flat. The spectral phase, $\phi(\omega)$, is extracted using the right-hand side of equation (16), but the product $u(t) \times \mathcal{J}^{-1}[f(\omega)]$ is replaced in equation (13) with:

$$\eta(t:f(\omega)) = \begin{cases} \mathcal{J}^{-1}[f(\omega)], & t \geq 0 \\ \mathcal{J}^{-1}[f_{NR}(\omega)], & t < 0 \end{cases} \quad (17)$$

where $f_{NR}(\omega)$ is the nonresonant component of the response. This modification is motivated by the fact that when the NRB is not flat, its Fourier transform, $\mathcal{J}^{-1}[\chi_{NR}(\omega)]$, is a symmetric function, centered about time zero with a finite width. Thus, the term $\eta(t:f(\omega))$ is used rather than $u(t) \mathcal{J}^{-1}[f(\omega)]$, assuming that the signal has a negative-time component arising solely from the nonresonant response, and that the positive-time response contains both resonant and nonresonant components.

FIG. 12 (b) illustrates a temporal function $\eta(t:\ln|\chi(\omega)|)$ obtained by the modified time-domain constraint shown in equation (17). More specifically, FIG. 12 (b) shows $\eta(t:\ln|\chi(\omega)|)$, as calculated from the simulated data of FIG. 12 (a). By way of comparison, the function $u(t) \mathcal{J}^{-1}[\ln|\chi(\omega)|]$ is plotted in the inset. The temporal function $u(t) \mathcal{J}^{-1}[f(\omega)]$, obtained without NRB information is shown in the inset of FIG. 12 (b). The time-domain representations in the main figure and in the inset are used to calculate two different estimations of $\phi(\omega)$ and subsequently to calculate complex third-order susceptibility $\chi(\omega)=|\chi(\omega)|\exp[i\phi(\omega)]$, tract the corresponding imaginary part, $\text{Im}\{\chi(\omega)\}=|\chi(\omega)|\sin[\phi(\omega)]$.

The resulting Raman spectra are shown in FIG. 12 (c) and its inset, respectively. In FIG. 12 (c) (inset) Raman spectrum extracted using $u(t) \mathcal{J}^{-1}[f(\omega)]$ from the inset of FIG. 12 (b) is shown. In FIG. 12 (c) (top), the extracted Raman spectrum (solid) and the reference Raman spectrum (dashed) are shown. FIG. 12 (c) (bottom) illustrates the difference between the reference and retrieved Raman spectra.

Figure 13A:
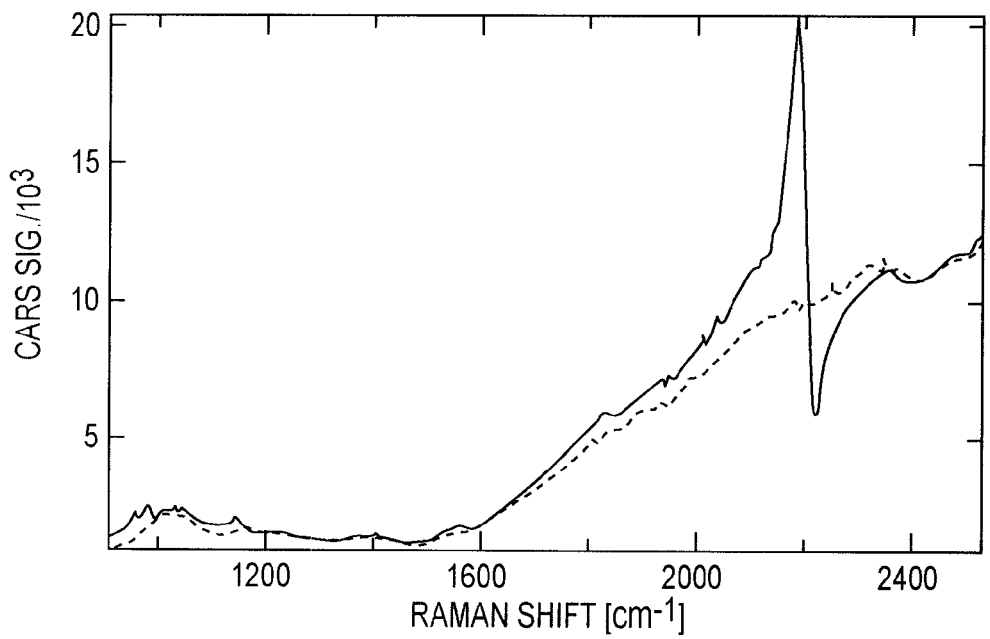
FIG. 13 (a) illustrates experimental CARS spectrum of benzonitrile in ethanol (solid) and a separately measured nonresonant background (dotted).
Figure 13B:
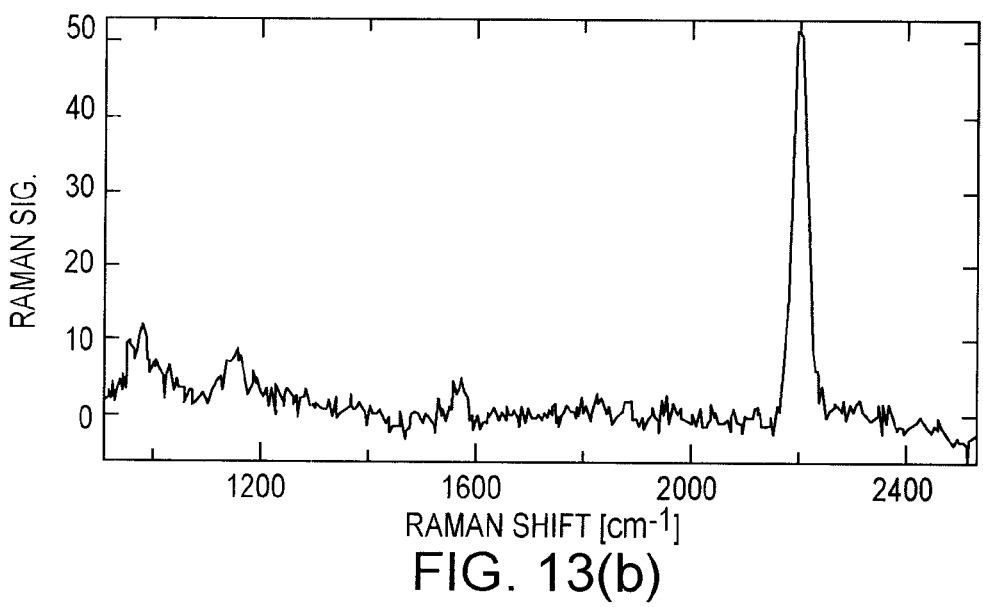

Experimental verification of this approach is demonstrated in FIG. 13. FIG. 13 (a) illustrates experimental CARS spectrum of benzonitrile in ethanol at a concentration of 1 M (solid) and a separately measured nonresonant background (dotted). The retrieved Raman spectrum is shown in FIG. 13 (b). In FIG. 13 (b), Raman spectrum extracted using equations (16) and (17) and the separately measured background are shown. Note that all the peaks in the vicinity of 1000, 1180, and 1600 cm$^{-1}$ are faithfully retrieved, even though their presence is not obvious in the original data.

The present invention and particularly the various preferred methods and strategies described herein, based on the CARS technique, allow for high sensitivity, chemical selectivity, no necessity of labeling nor staining, great penetration depth, high spatial resolution, etc. These advantages can be greatly beneficial to various fields of sciences and engineering of biology and materials. One of the most promising applications is intracellular live cell imaging, wherein one would monitor the chemical and physical responses of cells to external environment changes, such as chemicals, temperature, surface morphology, etc. Additional benefits can be realized in applications using conventional vibrational spectroscopy. Another important area that this invention will impact is wafer inspection for microelectronics. Spontaneous Raman microscopy is currently used as an integral part of wafer inspection. The present invention will provide a strategy for CARS microscopy to supplant spontaneous Raman microscopy as a tool of choice for this task. Additional areas expected to be impacted by this invention include, but are not limited to, early stage diagnosis of cancers, e.g. with endoscopy, stem cell differentiation, biocompatibility of biomaterials, wafer inspection for microelectronics, phase and morphology of soft materials, and physics and chemistry of composite materials.

The need for label-free chemical imaging is unquestionable in biology and materials sciences. The relative simplicity of the preferred embodiment systems and methods, and associated ease of operation, will lower the barrier for commercialization of targeting biomaterials and tissue engineering, biomedical imaging and materials characterization industries as well as fundamental sciences and engineering. The relative simplicity of the preferred systems and methods render them attractive candidates for commercialization.

Current research in biology and materials largely depends on optical imaging to understand the mechanisms of observed phenomena of interest. However, the needs for labeling and staining limit observable information significantly. The technology to provide non-invasive label-free chemical imaging of intracellular media will greatly enhance biomedical and tissue engineering research. The bio-imaging metrologies made feasible by the various preferred techniques described herein will result in significantly increased activity in intracellular chemical imaging. And, the increased sensitivity of the methods over spontaneous Raman microscopy will also be a great benefit to materials characterization in such areas as microelectronics.

Many other benefits will no doubt become apparent from future application and development of this technology.

All patents, published applications, and articles noted herein are hereby incorporated by reference in their entirety.

It will be understood that any one or more feature, component, or operation of one embodiment described herein can be combined with one or more other features, components, or operation of another embodiment. Thus, the present invention includes any and all combinations of components or features of the embodiments described herein.

As described herein above, the present invention solves many problems associated with previous type systems and methods. However, it will be appreciated that various changes in the details, materials and arrangements of components and operations, which have been herein described and illustrated in order to explain the nature of the invention, may be made by those skilled in the art without departing from the principle and scope of the invention, as expressed in the appended claims.

What is claimed is:

1. A system for producing a coherent anti-Stokes Raman scattering (CARS) signal associated a medium, the system comprising:
   an array for producing a first optical pulse carrying a pump field and a Stokes field, and a second optical pulse carrying a probe field;
   a first element for pulse-shaping the second optical pulse to suppress nonresonant background contribution to CARS;
   a second element for directing the first and second optical pulses to a focal volume of a medium such that a CARS signal is produced; and
   a detector for detecting a separated CARS signal from the focal volume in the medium.

2. The system of claim 1 wherein the first optical pulse is provided by continuum generation from an optical fiber and the first optical pulse has a spectral bandwidth of at least 2000 $cm^{-1}$.

3. The system of claim 1 wherein the first optical pulse is compressed such that the first optical pulse has a pulse duration in the range of from about 5 to about 100 femtoseconds.

4. The system of claim 1 wherein the first element for pulse-shaping the second optical pulse includes a pulse shaper and a controller for controlling phases and intensities of individual frequency components of the second optical pulse.

5. The system of claim 4 wherein the controller for controlling phases and intensities of individual frequency components of the second optical pulse includes a spatial light modulator.

6. The system of claim 4 wherein the controller for controlling phases and intensities of individual frequency components of the second optical pulse includes an optical medium that changes optical phases of specific frequency components of the second optical pulse.

7. The system of claim 6 wherein the optical medium is a phase compensating glass plate of about 0.01 to 3 mm thick and the phase of specific frequency components is determined by rotating the glass plate.

8. The system of claim 4 wherein the controller for controlling phases and intensities of individual frequency components includes a neutral density filter having a predetermined optical density in the range of 0 to 2.

9. A method for producing a coherent anti-Stokes Raman scattering (CARS) signal associated with a medium, the method comprising:
   producing a first optical pulse carrying a pump field and a Stokes field;
   producing a second optical pulse carrying a probe field;
   shaping the second optical pulse to suppress nonresonant background contribution to CARS and produce a shaped second optical pulse;
   directing the first optical pulse and the shaped second optical pulse to a focal volume to produce a CARS signal; and
   detecting the separated CARS signal from the focal volume in the medium.

10. The method of claim 9 wherein producing the first optical pulse is performed by continuum generation from an optical fiber and the spectral bandwidth of the first optical pulse is at least 2000 $cm^{-1}$.

11. The method of claim 9 wherein producing the first optical pulse includes compressing the first optical pulse to have a pulse duration in the range of from about 5 to about 100 femtoseconds.

12. The method of claim 9 wherein producing the second optical pulse includes directing the second optical pulse through a pulse shaper and controlling phases and intensities of individual frequency components of the second optical pulse.

13. The method of claim 12 wherein controlling phases and intensities of individual frequency components of the second optical pulse comprises:
   dividing the input optical pulse into multiple spectral groups;
   setting the relative phases of the multiple spectral groups either zero degree (in-phase) or 180 degrees (out-of-phase) to each other; and
   modifying the intensities of the multiple spectral groups such that the sum of the electric field envelopes of the multiple spectral groups becomes zero.

14. The method of claim 13 wherein multiple spectral groups comprise a first and a second transform-limited group that are located at the same center frequency and have different bandwidths and amplitudes (ps-fs scheme), the first transform-limited group having a narrow spectral bandwidth from about 1 to about 10 $cm^{-1}$ and the second transform-limited group having a broad spectral bandwidth from about 50 to about 500 $cm^{-1}$, wherein the phase difference between the first and the second transform-limited groups is 180 degrees.

15. The method of claim 13 wherein multiple spectral groups comprise a first and a second transform-limited group that have the same bandwidths and amplitudes but the center frequencies are separated from each other.

16. The method of claim 15 wherein the bandwidth of the first and the second transform-limited groups is in a range of from about 1 $cm^{-1}$ to about 10 $cm^{-1}$.

17. The method of claim 15 wherein the center frequencies of the first and the second transform-limited groups are separated by a frequency of from about 2 $cm^{-1}$ to about 30 $cm^{-1}$.

18. The method of claim 15 wherein the center frequencies of the first and the second transform-limited groups exhibit a phase difference of 180 degrees.

19. The method of claim 12 wherein controlling phases and intensities of individual frequency components of the second optical pulse includes passing the second optical pulse through a spatial light modulator.

20. The method of claim 12 wherein controlling phases and intensities of individual frequency components of the second optical pulse includes passing the second optical pulse through an optical medium that changes optical phases of specific frequency components of the second optical pulse.

21. The method of claim 20 wherein the optical medium is a phase compensating glass plate and optical phases of specific frequency components of the second optical pulse are changed by rotating the glass plate.

22. The method of claim 12 wherein controlling phases and intensities of individual frequency components includes passing the second optical pulse through a neutral density filter having a predetermined optical density in the range of 0 to 2.

23. The method of claim 12 wherein controlling phases and intensities of individual frequency components comprises blocking fractions of the dispersed light at unwanted frequency ranges.

24. The method of claim 9 wherein the CARS signal includes NRB, the method further including:
    allowing at least a portion of the NRB to remain in the CARS signal along with a resonant signal and a nonresonant signal;
    applying a Kramers-Kronig-based signal processing algorithm to post-process the CARS signal to thereby separate the resonant signal from the nonresonant signal.

25. The method of claim 24 wherein the Kramers-Kronig-based signal processing algorithm uses a modification of the time-domain representation of the CARS spectrum, substituting the negative-time component of a time-domain representation of a NRB spectrum in place of the negative-time component of the CARS spectrum to be analyzed, and subsequently transforming back to the spectral domain.

* * * * *